(12) United States Patent
Elson et al.

(10) Patent No.: US 7,160,277 B2
(45) Date of Patent: Jan. 9, 2007

(54) MALE URINARY INCONTINENCE SHEATH HAVING GEL ADHESIVE AND ELASTIC SECUREMENT TAPE

(75) Inventors: Edward E. Elson, Anaheim, CA (US); Paul Dwork, Camarillo, CA (US); Joshua Dwork, Camarillo, CA (US)

(73) Assignee: Leading Edge Innovations, Inc., Camarillo, CA (US)

( * ) Notice: Subject to any disclaimer, the term of this patent is extended or adjusted under 35 U.S.C. 154(b) by 0 days.

(21) Appl. No.: 11/342,062

(22) Filed: Jan. 27, 2006

(65) Prior Publication Data

US 2006/0122568 A1    Jun. 8, 2006

Related U.S. Application Data

(60) Division of application No. 10/868,289, filed on Jun. 14, 2004, which is a continuation-in-part of application No. 10/705,187, filed on Nov. 10, 2003, now abandoned.

(51) Int. Cl.
*A61F 5/443* (2006.01)
*A61F 5/453* (2006.01)

(52) U.S. Cl. ........................... 604/352; 604/349

(58) Field of Classification Search ........ 604/346–356, 604/307; 128/760; 606/201
See application file for complete search history.

(56) References Cited

U.S. PATENT DOCUMENTS

| | | | |
|---|---|---|---|
| 3,788,324 A | 1/1974 | Lim | |
| 3,835,857 A * | 9/1974 | Rogers et al. | 604/349 |
| 3,863,638 A | 2/1975 | Rogers, III et al. | 128/295 |
| 4,187,851 A | 2/1980 | Hauser | 128/295 |
| 4,378,018 A * | 3/1983 | Alexander et al. | 604/350 |
| 4,475,909 A | 10/1984 | Eisenberg | 604/349 |
| 4,534,767 A | 8/1985 | Habib | |
| 4,540,409 A | 9/1985 | Nystrom et al. | 604/349 |
| 4,576,599 A | 3/1986 | Lipner | |
| 4,588,397 A | 5/1986 | Giacalone | 604/349 |
| 4,626,250 A | 12/1986 | Schneider | 604/352 |
| 4,650,817 A | 3/1987 | Allen, Jr. et al. | |
| 4,759,753 A | 7/1988 | Schneider et al. | 604/352 |
| 4,784,655 A | 11/1988 | Campion et al. | 604/349 |
| 4,790,834 A | 12/1988 | Austin | 604/349 |
| 4,865,595 A | 9/1989 | Heyden | 604/352 |
| 5,009,649 A | 4/1991 | Goulter et al. | 604/351 |

(Continued)

FOREIGN PATENT DOCUMENTS

GB    2126483 A    3/1984

(Continued)

*Primary Examiner*—Tatyana Zalukaeva
*Assistant Examiner*—Laura C. Hill
(74) *Attorney, Agent, or Firm*—Koppel, Patrick & Heybl; Michael J. Ram

(57) ABSTRACT

A male urinary incontinence device comprises a cylindrical sheath with an open first end to receive the penis and a tubular connector at a second end for discharge of collected urine, the sheath having a longitudinal opening along at least one side to allow ready placement of the penis therein. A viscous gel strip is applied to the upper inner circumference of the sheath and an elastic strap is applied to the upper outer circumference of the sheath the gel strip and strap acting cooperatively to retain the sheath on the penis and to render the sheath leak proof in use. The sheath also includes a connector assembly for attachment of tubing and a urine collection vessel. Placement of the device may also include a mounting ring and a strap assembly.

14 Claims, 23 Drawing Sheets

U.S. PATENT DOCUMENTS

| | | | |
|---|---|---|---|
| 5,065,459 A | 11/1991 | Tjahaja et al. | 4/144 |
| 5,336,211 A | 8/1994 | Metz | 604/352 |
| 5,423,784 A | 6/1995 | Metz | 604/351 |
| 5,531,725 A | 7/1996 | Steer | 604/349 |
| 5,618,277 A | 4/1997 | Goulter | 604/349 |
| 5,643,235 A | 7/1997 | Figuerido | 604/352 |
| 5,716,350 A | 2/1998 | Ryan | 604/385.1 |
| 5,752,944 A | 5/1998 | Dann et al. | 604/352 |
| 5,797,890 A | 8/1998 | Goulter et al. | 604/351 |
| 6,007,524 A | 12/1999 | Schneider | 604/327 |
| 6,010,489 A | 1/2000 | Blackburn | 604/353 |
| 6,039,750 A * | 3/2000 | Kubalak et al. | 606/201 |
| 6,068,618 A | 5/2000 | Anderson | 604/349 |
| 6,113,582 A | 9/2000 | Dwork | 604/349 |
| 6,200,195 B1 * | 3/2001 | Furuno et al. | 450/81 |
| 6,248,096 B1 * | 6/2001 | Dwork et al. | 604/349 |
| 6,479,726 B1 * | 11/2002 | Cole | 604/358 |

FOREIGN PATENT DOCUMENTS

| | | | |
|---|---|---|---|
| JP | 08-010279 | * | 1/1996 |

* cited by examiner

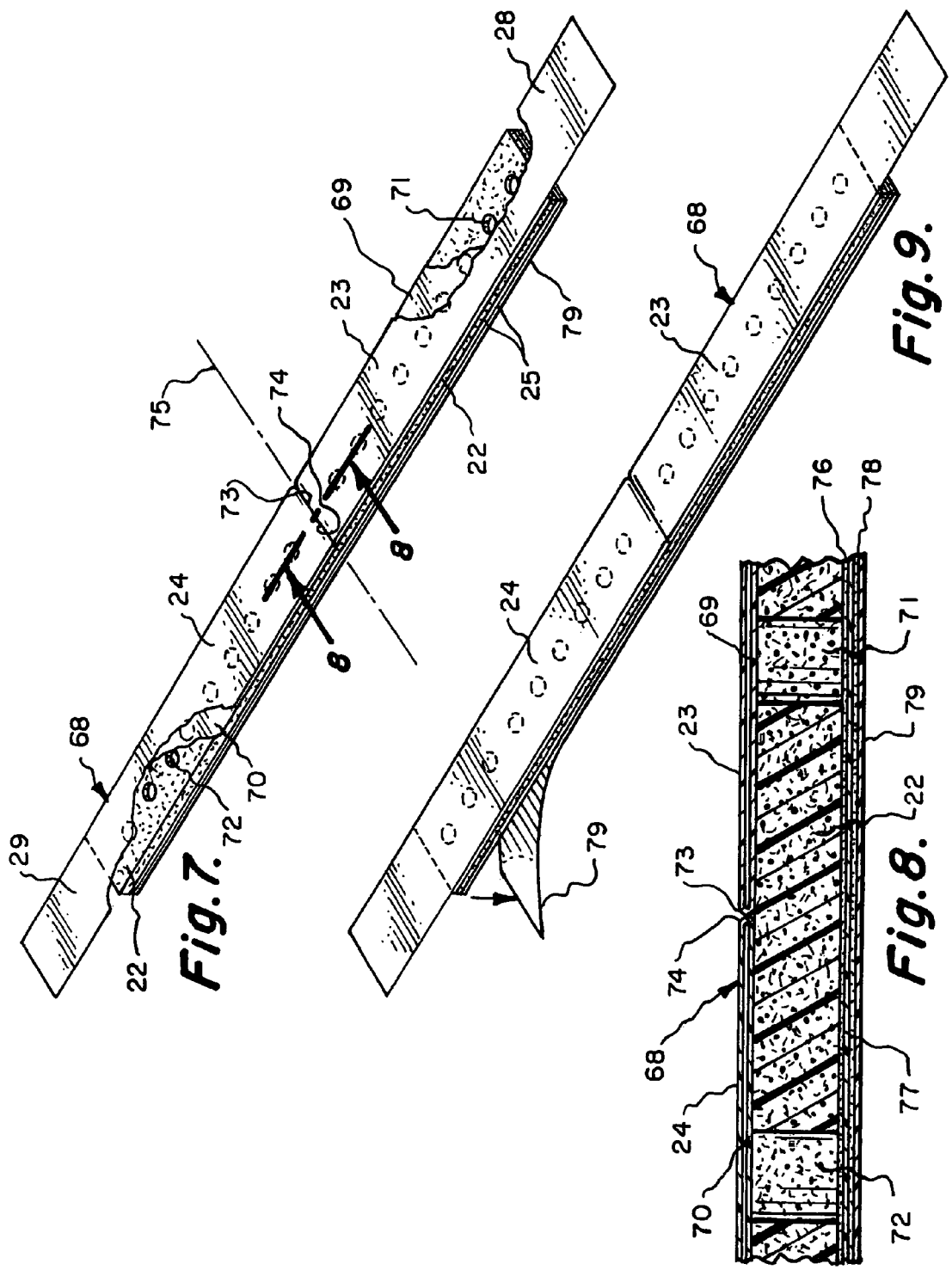

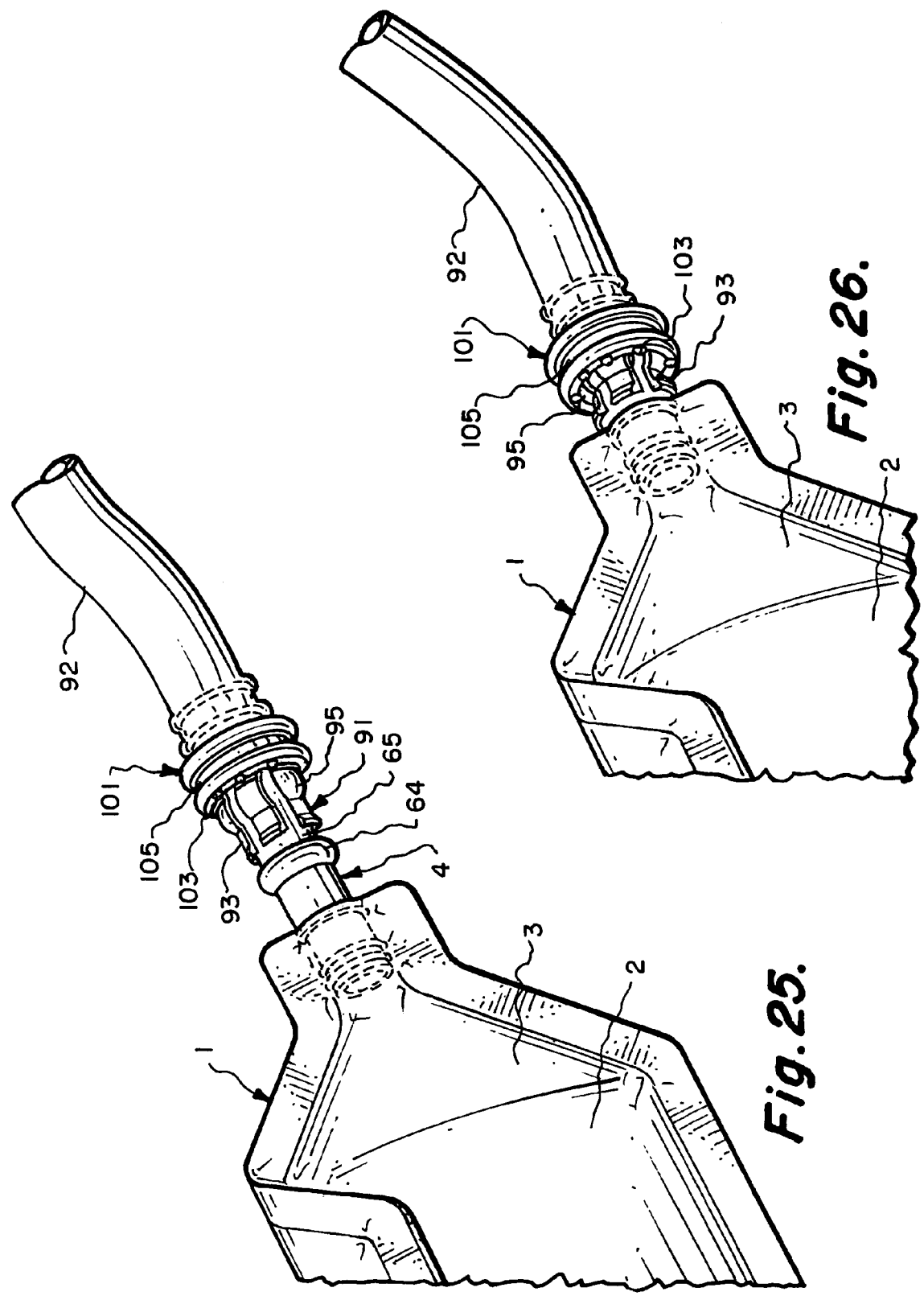

MALE URINARY INCONTINENCE SHEATH HAVING GEL ADHESIVE AND ELASTIC SECUREMENT TAPE

This is a Divisional of U.S. patent application Ser. No. 10/868,289, filed Jun. 14, 2004, which is a Continuation-in-Part of U.S. patent application Ser. No. 10/705,187, filed Nov. 10, 2003, now abandoned.

BACKGROUND OF THE INVENTION

1. Field of the Invention

The present invention is directed to a device and related accessories for use by incontinent males and, more specifically, a device which both fits over and around the penis.

2. Background

Urinary Incontinence (UI) is a problem estimated to afflict about 4 million men in the United States. Another 9 million US females also suffer from incontinence. The annual cost of providing care for persons with UI is estimated to be in excess of $16 billion. The market for adult absorbent devices or diapers alone is in excess of $2 billion and continues to grow. A shift to a healthier, more active and older population and a society which is increasingly mobile is resulting in an increasing number of persons suffering from incontinence, and a demand from that population for more effective and reliable solutions for UI.

UI can affect persons of all ages, and may be the result of physical disability or a psychological condition. There are several different types of incontinence. Acute (or Transient) Incontinence is caused by generally treatable medical problems. Medical conditions such as dehydration, delirium, urinary retention, fecal impaction/constipation, and urinary tract infection can cause an onset of UI. Additionally, certain medications can cause or contribute to an incontinence problem, such as anticholinergic agents, antihistamines, antidepressants (TCA), phenothiazines, disopyramides, opiates, antispasmodics, Parkinson drugs, alpha-adrenergic agents (high blood pressure drugs), sympathomimetics (decongestants), and sympatholytics (e.g., prazosin, terazosin, and doxazosin).

Chronic UI is conventionally classified into four groups: Stress, Urge, Overflow, and Functional incontinence. They may occur alone or in combination, the latter being more common as the patient ages. Chronic UI is persistent and more difficult problem to treat.

Stress incontinence is the involuntary leakage of small amounts of urine resulting from an increased pressure in the abdomen. Events which may result in such involuntary leakage include sneezing, coughing, laughing, bending, lifting, etc. While primarily a female problem, men also suffer from stress incontinence. Stress incontinence in men is typically the result of a weakened urethral sphincter that surrounds the prostate, frequently as a result of prostate surgery.

Urge incontinence, characterized by insufficient ability to prevent voiding once the urge to void arises, is most common in middle aged and older people. Detrunorm hyperreflexia or instability which is associated with disorders of the lower urinary tract or neurologic system is a common cause. However, urge incontinence can also be the result of urologic carcinoma, diverticula, or other physical abnormalities.

Overflow incontinence, which accounts for 10–15% of urinary incontinence, is usually the result of an obstruction. (e.g., enlarged prostate, urethral stricture) of the bladder outlet or an atonic bladder as the result of neurologic injury (e.g., spinal chord trauma, stroke), diabetic neuropathic bladder, or drug-induced atonia. The obstruction leads to bladder overfilling, resulting in a compulsive detrusor contraction. In this form of UI chronic "dribbling" is common. Drug induced atonia can be caused by anti-cholinergics, narcotics, anti-depressants, and smooth muscle relaxants.

Functional incontinence accounts for 25% of all incontinence. It occurs primarily when a person is confined and sedentary, such as in a nursing home or during a long period of convalescence. Functional incontinence is sometimes diagnosed as a result of the individual simply being unable to communicate his or her needs, or through other sensory impairments that make the individual unaware of his or her need to void. This condition can further result from decreased mental function, decreased functional status, and/or a simple unwillingness to physically go to the toilet.

Incontinence is also frequent among persons rehabilitating from stroke, head injury, multiple sclerosis, amputations, and spinal cord injury.

Nocturnal enuresis afflicts approximately 15–20% of school age children between the ages of 4 and 16. Most often, the reason a child or adult will have the problem of nocturnal enuresis is because they simply cannot wake up. Treatment of enuresis typically requires training the person to recognize the need to urinate during sleep, or to train the person to sleep correctly. Moisture sensing alarms have been successfully employed, but if soiled bedding is to be avoided, diapers, absorbent padding or other collection devices are required.

UI, or even the fear of an incontinent incidence, can lead to discomfort and embarrassment, and eventually to social withdrawal and isolation. Normal activities, social interaction, and sexual activity are often curtailed or avoided as a result. UI is the predominant reason aging parents are put into nursing homes.

Incontinence is typically treated by catheterization, use of absorbent products, and for males, devices attached to the exterior surface of the penis to collect urine discharge. Catheterization, whether intermittent or permanent, is an unacceptable approach in many instances and is the least preferred type of bladder management. The procedure is very inconvenient and many patients are psychologically averse to self-catheterization, or physically unable to perform the manipulations required. A major deficiency of either permanent or intermittent catheterization is that the urine of virtually every patient becomes contaminated by bacteria. Catheter-associated bacteria represent the most common infection acquired in acute care and long-term care facilities. Complications ranging from bladder spasms and catheter leakage to death caused by septicemia are also well known limitations. Bacterial entry into the bladder occurs either from extra luminal migration along the outside of the catheter, contamination on insertion of the catheter, or contamination of the drainage bag, leading to bacterial growth and subsequent migration into the bladder.

Diapers and other absorbent constructions are the most popular remedy because they are easily obtained, and can address acute UI symptoms quickly. However, while affording reasonably effective control of urine leakage and providing mobility to the patient, absorbents also have very serious drawbacks. A major deficiency is that urine is not removed from the genital region. The absorbents merely collect and disperse the urine and maintain a moist environment with the urine typically remaining in contact with skin surfaces, causing irritation and discomfort. While improved constructions with different absorbent layers attempt to direct the urine to a region away from the skin and minimize contact, the resulting benefit is less then desired.

Absorbent devices also require a large area of absorbent material surrounded by water proof external barriers, usually in the form of pants or diapers. Such an arrangement when dry is uncomfortable to the wearer. When wet the discomfort level increases greatly and the wearer must deal with the distinctive, embarrassing odor of urine. Once removed, whether soiled or not, the disposable-type diaper usually must be disposed of, creating the need to always carry a supply of such absorbent devices.

In men, an alternative to the indwelling catheter or absorbent device is an external collecting device that is fitted over the male genitalia, like a condom. This may include an absorbent material or can be connected by a tube to a drainage bag that is typically held onto the thigh by leg straps. In a non-ambulatory situation, bedside drainage bags can be used. Many such "external catheter" devices are described in the prior art. Alternatively, rather then being attached to an external bag, the sheath may have an enlarged integral, drainable lower portion for collecting the urine. Typically such devices include some means to keep the urine in the collection portion separated from the penile tissue. The condom or sheath portion is usually fabricated from a latex, silicone or similar flexible, non-porous film material. These devices, are normally provided in a rolled-up or folded state and are unrolled or everted onto the penis and then sealingly engaged in some manner to the penis. Alternatively the sheath may be formed by rolling a sheet material around the penis and then sealing the opening along the length and to the penis such as is shown in U.S. Pat. No. 6,113,582 to Dwork, one of the inventors of the present device. Sealing the condom-like sheath to the penis may be accomplished by a two-faced adhesive strip within the upper end of the sheath that is applied to the penis The sheath may additionally be held to the penis by an external band which surrounds the sheath and is secured using a VELCRO® hook and loop fasteners. An attaching ring may also be mounted on an undergarment to secure the top of the sheath. As a further alternative a strap structure may be applied around the user's waist. Other structural features which may be included are accordion like pleats to allow the sheath to expand should the wearer experience an erection or to accommodate a different size flaccid penis.

These devices have numerous disadvantages in their use. They may be too complex to apply and they must be properly sized for the device to function properly without leaking, falling off or restricting normal blood flow to the penis. The application of the condom member requires some degree of dexterity to position and unroll the condom onto the penis, which is frequently flaccid. The flaccid state of the penis renders the seal created by the condom often ineffective, and frequently inadequate. Frequently, the issue of device sizing creates difficulties, because of variability between individuals or daily size variations in a single individual.

A further serious disadvantage with this type of device is that a blockage in the drainage tube or in the connection between the tube and the sheath will cause a back-up of urine in the condom causing the sheath to leak, break, or slip from the penis. Such events can be extremely messy and embarrassing as urine is inadvertently discharged from the sheath wetting the user's clothing and creating an aroma problem. Still further, constant contact between the external penile surface and urine can result in severe irritation of the external tissue as well as provide an entry path for bacterial infection of the urinary tract.

Other devices comprise loose-fitting sleeves for the penis, such as the McGuire style male urinal. The urinal, which is in effect a bag into which the penis extends, is used in conjunction with a valve tube leading to a leg bag. In theory, the urinal drains into the leg bag. These devices also have problems with poor sealing and spillage of urine and a flaccid penis may withdraw from the upper opening of the device. Still further, because the device relies on gravity to feed urine from the urinal to the leg bag, the urine will not drain properly when an individual is in a sitting or prone position.

SUMMARY OF THE INVENTION

The male incontinence devices described herein, which incorporate features of the invention, provide a means of handling male urinary incontinence that overcomes the problems of the prior devices. The invention permits an individual or a care giver to easily place the device onto any sized male member, within a specified range, without the need for the application of any force to stretch or deform the device while applying it, even if the penis is flaccid and withdrawn, and provides a positive seal while generally isolating the external penile tissue and surrounding skin from prolonged contact with urine. The devices also provide compensation for changes in penile length and diameter over time by providing flexibly compliant portions engaging the penile shaft.

According to the invention, a fluid impervious wrap or pocket is provided which allows the formation of a fluid tight, flexible and expandable sheath around the penis of a user. The sheath that is formed has an open proximal end position including an open longitudinal flap portion above the top of the penile sheath, and a distal end for drainage or attachment of a collection device, such as an external urine bag or a leg mounted collection bag. The sheath structure, once placed over the head of the penis, is manually sized to circumferentially envelop and effect a fluid-tight seal about at least a portion of the length of the penis proximal to the glans of a user with the flap portion overlapping and releasably attached to the remainder of the outer surface of the device, providing a first fluid-tight seal to the penile sheath. Use of low tension elastic materials of construction for at least some of the components of the device allows for expansion of the assembled sheath without leakage or disruption of the seals within the assembled sheath or to the penis.

The invention also incorporates a method of forming and assembling devices incorporating features of the invention.

Still further, the invention includes a unique new coupling device for attaching a drainage tube or other collection devices to the male incontinence device. However, the utility of the connection device is not limited to use with the male incontinence device herein described. It may be used for the attachment of any number of tubular devices, indwelling catheters or other collection means to create a readily connected and disconnected, leak free liquid flow path between devices. The coupling device may be provided with an internally mounted one-way check valve. The coupling device may also be provided with a collar which may in a first position, permit connection and disconnection, and in a second position prevent connection or disconnection.

Still further, the invention includes a unique gel seal assembly with means to ensure that it is applied in a gap free manner and thus provide a continuous seal preventing fluid leakage.

Still further, the invention includes multi-loop strap means which allow for ready attachment and adjustment for penile length of the sheath of the invention to a plate secured to the patient by means of an adjustable waist belt.

BRIEF DESCRIPTION OF THE DRAWINGS

The foregoing and other features and advantages of the present invention will be more fully understood from the following detailed description of an illustrative embodiment, taken in conjunction with the accompanying drawing in which:

FIG. 7 is an isometric view of a gel strip assembly for attachment to the device of FIG. 2 or FIG. 3 having a portion of one element cut away to expose the layer below.

FIG. 8 is an enlarged, partial sectional view taken along line 8—8 of FIG. 7.

FIG. 9 is an isometric view of the gel strip assembly of FIG. 7 depicting the removal of a strip of a protective release liner from its bottom surface to expose an adhesive coating for bonding to the cut sheet of FIG. 2 or FIG. 3.

FIG. 25 is an isometric view of the locking ring of FIG. 23 positioned in its unlocked position on the female coupler of FIG. 22, further showing a length of tubing attached to the female coupling and a partial view of distal portion of the device of FIG. 1.

FIG. 26 is an isometric view of the locking ring of FIG. 23 positioned in its locked position on the female coupler of FIG. 22 after the female coupler has been mated to the male coupling device of FIG. 6.

DETAILED DESCRIPTION

Figure 1:
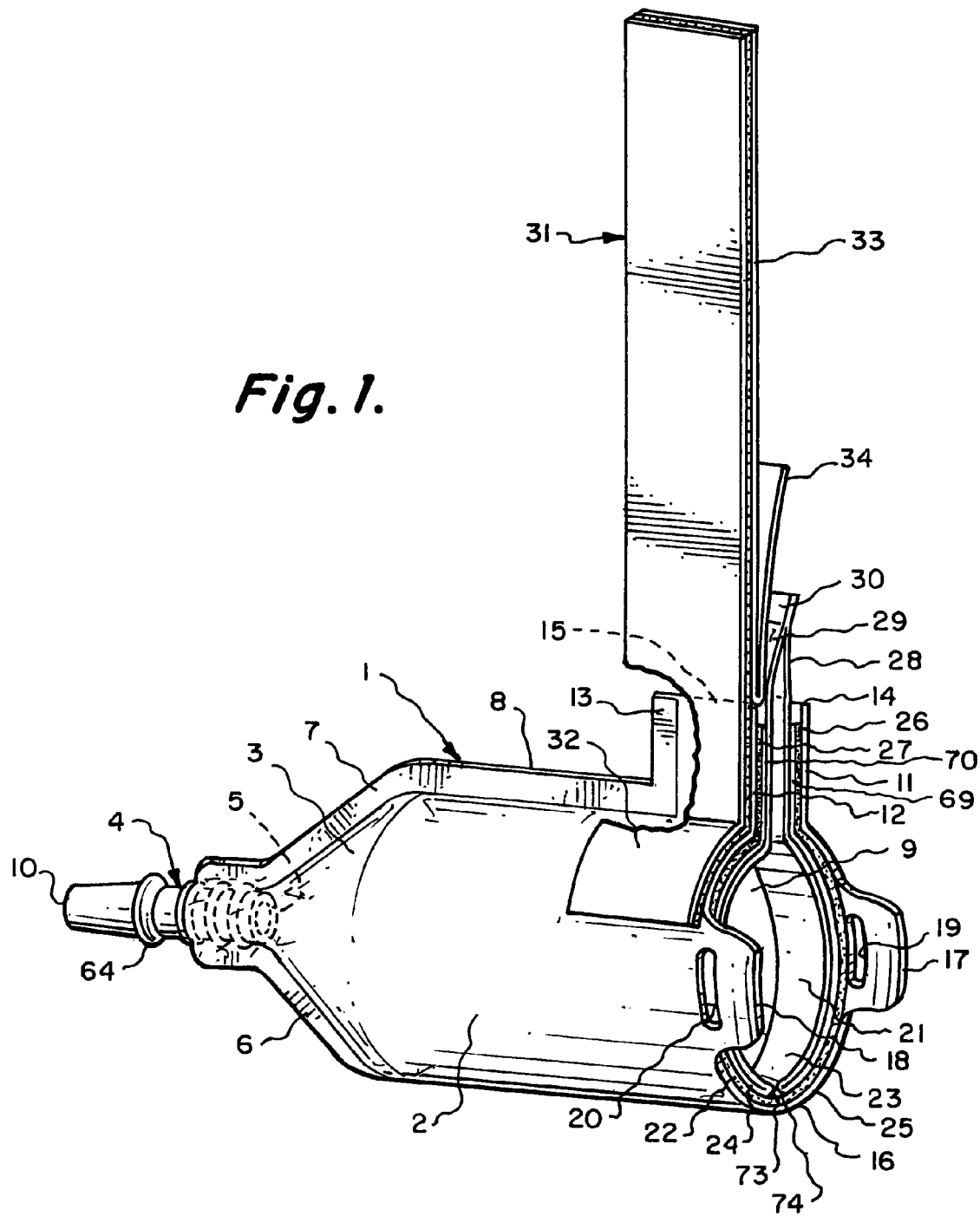
FIG. 1 is an isometric view of a first embodiment of a device incorporating features of the invention as it is ready to be secured to the penis of a user of the device, partially cutaway to show hidden features.

A first embodiment of an easily applied sheath type device 1 for use on incontinent males is shown in FIG. 1. The substantially cylindrical sheath body 2 is formed from a liquid (urine) impervious polymeric material. A method of manufacturing the sheath is described below with reference to FIGS. 2–13. The cylindrical section of sheath body 2 has a funnel shaped distal portion 3. A male coupling device 4 is secured in the distal end 5 of the funnel portion 3 in a liquid tight manner such as by heat sealing to the polymeric material. A lower heat sealed edge 6 merges with the distal end 5 of the funnel shaped portion 3. An upper heat sealed side edge 7 of the funnel shaped portion 3 of sheath device 1 extends from the heat sealed distal end 5 and merges with the upper, longitudinal heat sealed edge 8 of the cylindrical sheath body 2. The heat sealed portions identified above enable the flat sheet of material from which the incontinent device is formed to be a fluid-tight device with a first end opening 9, also referred to as a proximal opening, for receiving the penis of a user and a distal or second end opening 10 from which urine can be directed for storage or disposal.

The proximal end of the cylindrical sheath body 2 has a right hand flap 11 and a left hand flap 12 which extend vertically (as shown in FIG. 1) from an upper, unsealed area at the open end of the cylindrical sheath body 2. The distal, vertical edges of the two flaps are sealed together forming a heat sealed area 13 which is contiguous with the heat sealed edge 8. Heat sealing the various edges and areas of the flat sheet of material of sheath 1 as described above, result in the construction of a generally cylindrical sheath for enclosing the penis of a user to direct urine away from the body and into a collection device or other disposal means. The upper edges 14, 15 of the right and left hand flaps 11, 12 respectively are open (not sealed), allowing the right and left flaps 11, 12 to be used for grasping the sheath body 2 for placement on the penis and to provide a larger opening into which the penis can be readily placed.

Figure 37:
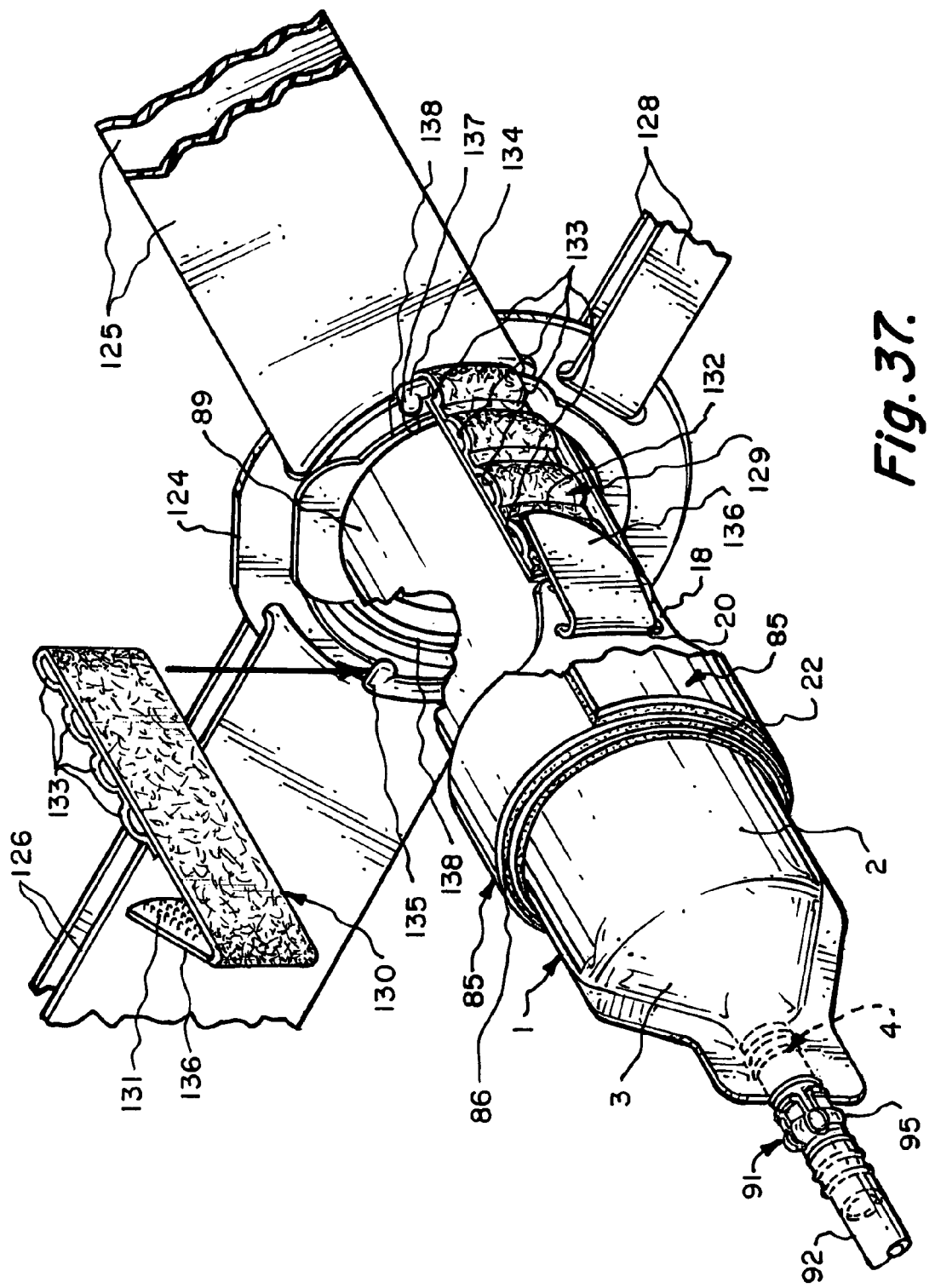
FIG. 37 is an isometric view of a faceplate retention ring and straps utilized to further secure the device of FIG. 1 to the body of an ambulatory patient.
Figure 38:
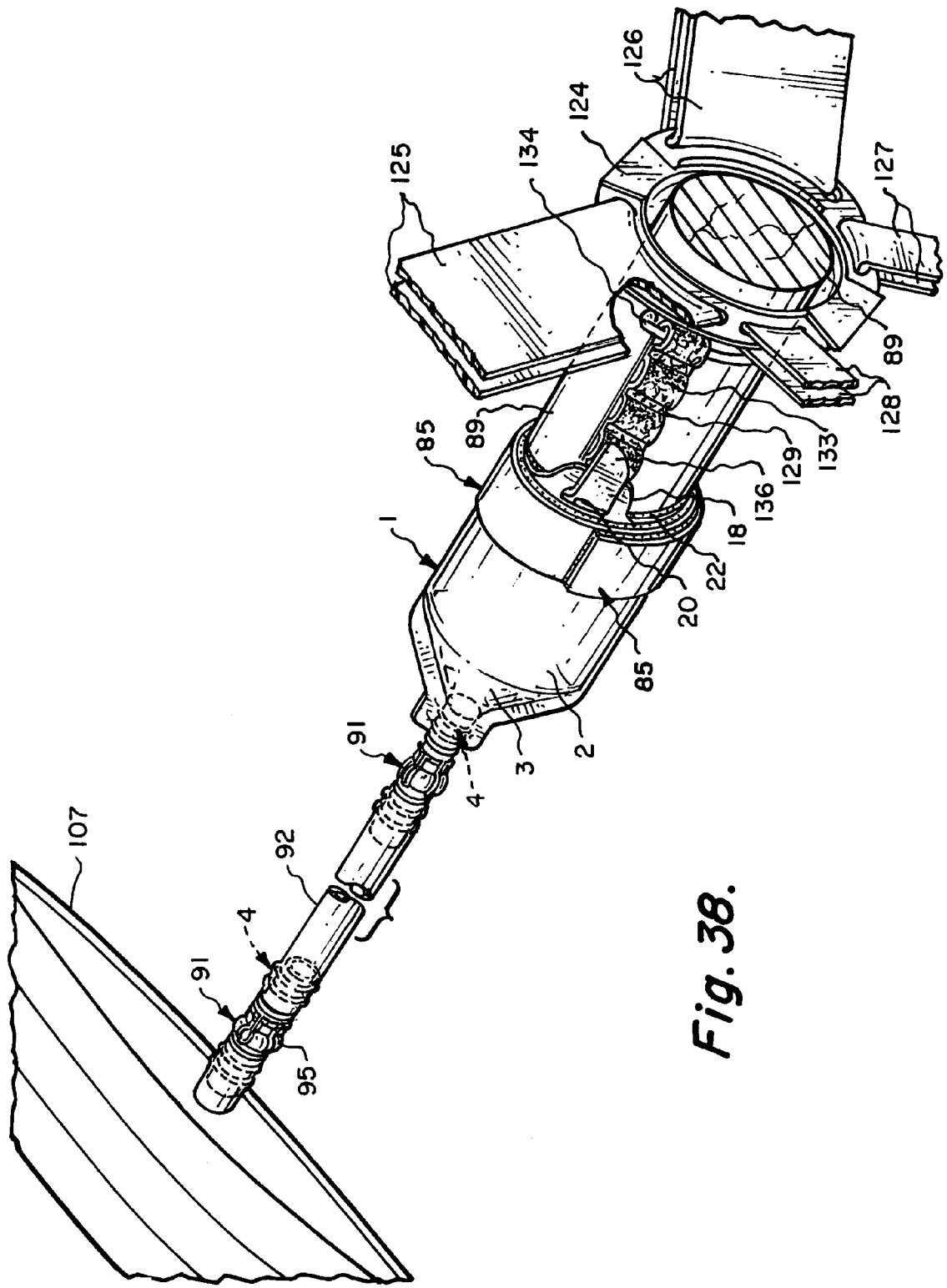
FIG. 38 is an isometric view of the device of FIG. 1 attached to the face plate of FIG. 37 and connected to a collection bag.

Integral with the edge 16 of the proximal opening 9 of the cylindrical sheath body 2 are two spaced apart tabs. The right side tab 17 and the left side tab 18 are formed with slots 19, 20 respectively to receive adjustable straps (omitted here for clarity) which attach to connectors on a retention plate mounted on a waist-encircling belt as depicted in FIGS. 37–38.

Located and adhesively affixed on the interior surface of the sheath body 2 (by removing a release liner and exposing an adhesive surface) and extending generally circumferentially and aligned with the proximal opening 9 of the cylindrical sheath body 2, is a gel strip assembly 21 comprising a compliant, viscous and stretchable polymeric gel strip 22, two folded strips of a release liner film (a removable barrier material), right half 23 and left half 24, releasably adhered to the inner surface of the gel strip 22 and a double-backed adhesive strip 25 with two different adhesives for permanently bonding the gel strip to the inner surface of sheath body 2. The gel strip assembly 21 is further described below and illustrated in FIGS. 7–9.

The two folded strips of release liner film 23, 24 which cover the surface of the gel strip 22 are provided to facilitate the insertion of the user's penis into the interior of the sheath body 2 by preventing the viscous gel from prematurely contacting and adhering to the shaft of the penis during its insertion into the sheath. Such unwanted adherence would make insertion of the penis into the sheath more difficult and possibly affect the integrity of the seal around the circumference of the penis provided by the gel strip. The two folded release liner film strips 23, 24 each have a patient side surface which contacts the penis of the user and a gel strip side in contact with the gel strip. The folded ends of each strip are positioned adjacent to each other at the center of the bottom of the proximal cylindrical opening of sheath body 2. The two release liner film strips 23, 24 are folded so that the gel strip sides are shorter in length than the patient contacting sides. The gel strip 22 halves are each coextensive with a half of the gel strip surface. The gel strip sides have perforations 71 to reduce the contact area to facilitate removal of the strips and to allow a predetermined area of the viscous gel strip to adhere to the undersides of the patient sides to prevent separation of the layers of release film which could otherwise interfere with insertion of the penis into the sheath.

The gel strip 22, in addition to extending around the inner circumference of the sheath body 2, has a right hand segment 26 and a left hand segment 27 which extend vertically and are bonded to right and left hand flaps 11, 12 respectively. These vertical segments terminate approximately 0.150 inches from the upper flap edges 14 and 15.

The longer, patient sides, right hand liner film side tab 28, and left hand liner film side tab 29, of the release liner film strips 23, 24, extend vertically beyond the two gel strip segments 26, 27 and beyond upper edges 14, 15 of the right and left hand sheath flaps 11, 12. The right and left hand sides 28, 29 of the patient side release liners 23, 24 are heat sealed together to provide a heat sealed tab 30, approximately 0.250 inches wide. The heat sealed tab 30 allows the user to grasp and remove the two release liners simultaneously as is described below.

Affixed to the outer surface of the adjacent proximal opening 9 of the sheath body 2 is an elastomeric, adhesive-backed tape strip assembly 31 of sufficient length to wrap completely around the circumference of the cylindrical body of the sheath. In the embodiment depicted in FIG. 1, the tape strip assembly 31 is shown adhered to the left side of the sheath body 2. It can alternatively be placed on the right side of the sheath body 2 without affecting its function. The adhesive-backed tape strip 31 is aligned with the edge of the proximal opening 9 and has a lower segment 32 approximately 1.0 inches long adhesively affixed to the outer surface of the sheath 2. The longer, upper segment of tape strip assembly 31 is covered by a removable release liner 33 on the reverse side having a portion thereof folded back on itself creating a release liner tab 34. The release liner is removed to expose the adhesive when it is desirable to wrap the tape around the circumference of the sheath to secure it to the penis of the patient. The adhesive is exposed by pulling on the release liner tab 34 which extends vertically upwards or outward past the upper edge 15 of left hand flap 12. The tape strip is described in greater detail in FIGS. 11–13 and 18–20. The tape strip assembly 31 is preferably wider than flaps 11 and 12 by approximately 0.25 inches so that after the adhesive is exposed, a liquid-tight barrier can be created distally to the gel strip following folding over of the flaps and stretching and wrapping the tape around the outer circumference of the sheath body 2.

Referring to FIGS. 2–13, the fabrication of a first embodiment of the invention is described. The starting material for fabrication of the sheath 1 is a flat film of a liquid impervious, flexible polymeric material, preferably soft-to-the-touch and non-allergenic. It is also preferred that the material is a thermoplastic so that it can be heat sealed. However, thermoset polymers can also be used and sealing accomplished by using room temperature or hot melt adhesives, RF sealing or other common attachment techniques. In the assembly procedure described below, heat sealing is referred to. However, any suitable sealing techniques can be used. Suitable materials include, but are not limited to silicone, polyvinylchloride, polyethylene, latex and synthetic rubber. A preferred material is a medical grade, designed for skin contact, 5 to 8 mil thick polyurethane film provided in sheets with a useable area of at least about 7 inches by 8 inches or roll stock from which similar sized sections can be separated.

Figure 2:
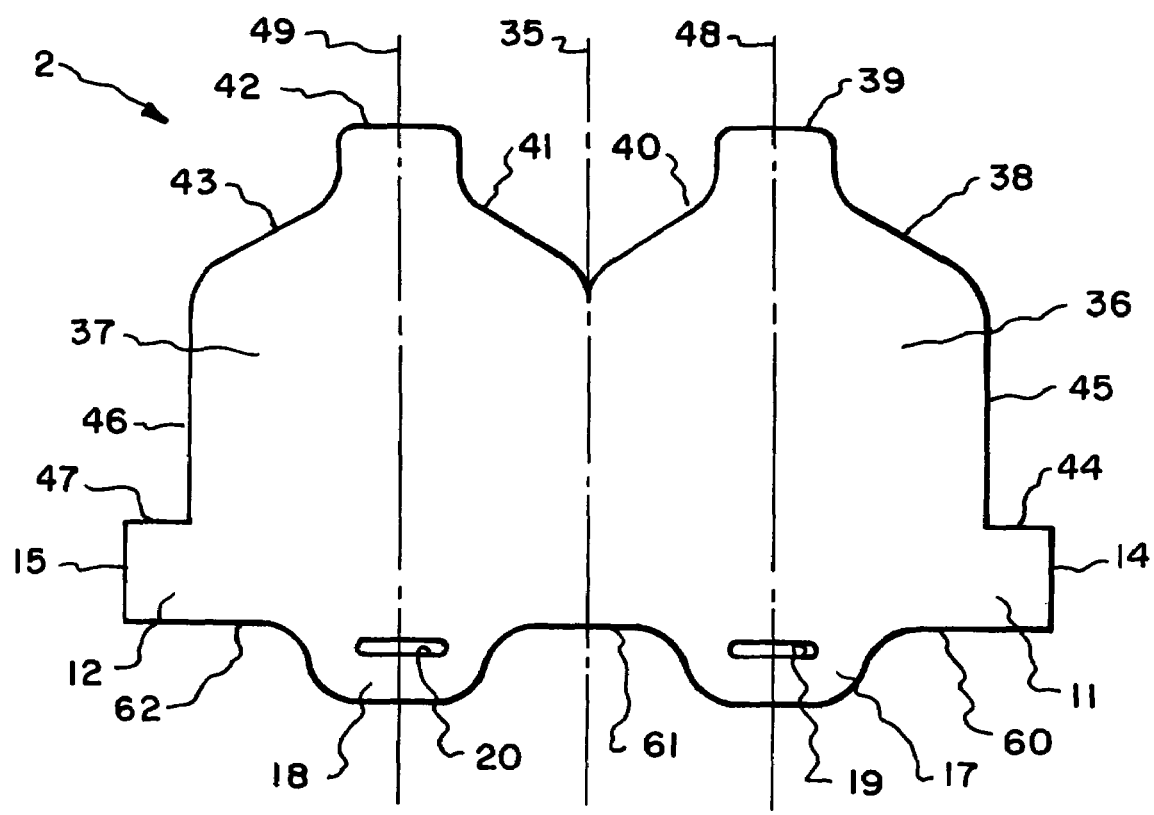
FIG. 2 is a plane view of a first stage in the fabrication of the device of FIG. 1 wherein a preferred shape is cut from a single sheet of elastomeric or polymeric material.

A first piece of the sheath body 2, such as shown in FIG. 2, is cut from the film by any technique known to the art such as die cutting, using a punch, laser cutting, etc. The first piece of the sheath body 2 after cutting has a number of landmarks useful in describing its construction into the sheath 1 of the present invention. In the preferred embodiment, the sheath body 2 is symmetrical about the longitudinal centerline 35 having a right side section 36 and a left side section 37. The distal edges 38, 39, 40, 41, 42, 43 and the side edges 44, 45, 46, 47, constitute mating elements which are aligned and heat sealed to form the sheath 1. The upper edges 14, 15 of the right hand flap 11 and the left hand flap 12 respectively, are left unsealed except for a short section of the adjacent edges 44, 47 as is shown in greater detail in FIG. 10. The right side and left side tabs 17, 18 are left unsealed as are the three collinear proximal edges 60, 61, 62. The right hand section 36 and left hand section 37 are not symmetric about their respective centerlines 48, 49. Slots 19 and 20 are cut at the same time as is the sheath body 2.

Figure 3:
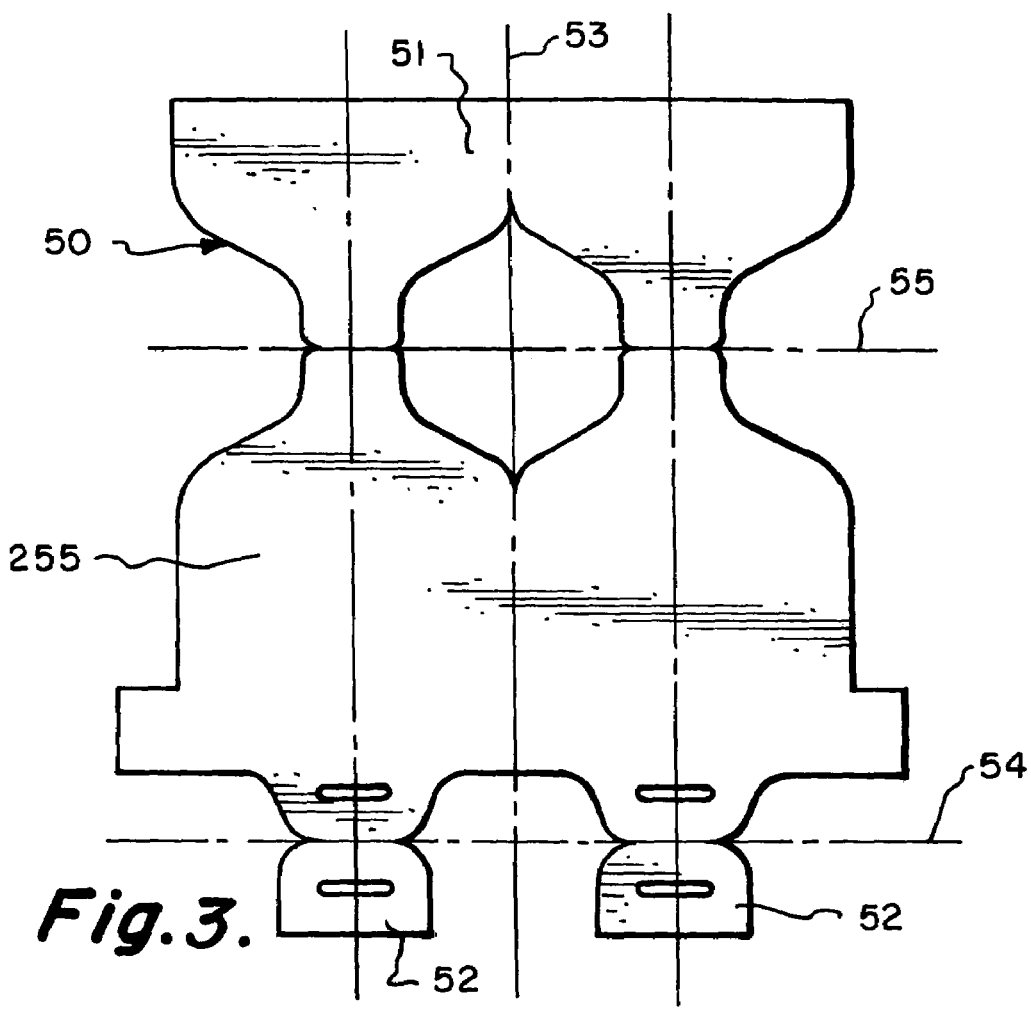
FIG. 3 is a plane view of an alternate configuration of FIG. 2 wherein additional material has been provided in order to reinforce portions of the device.
Figure 4:
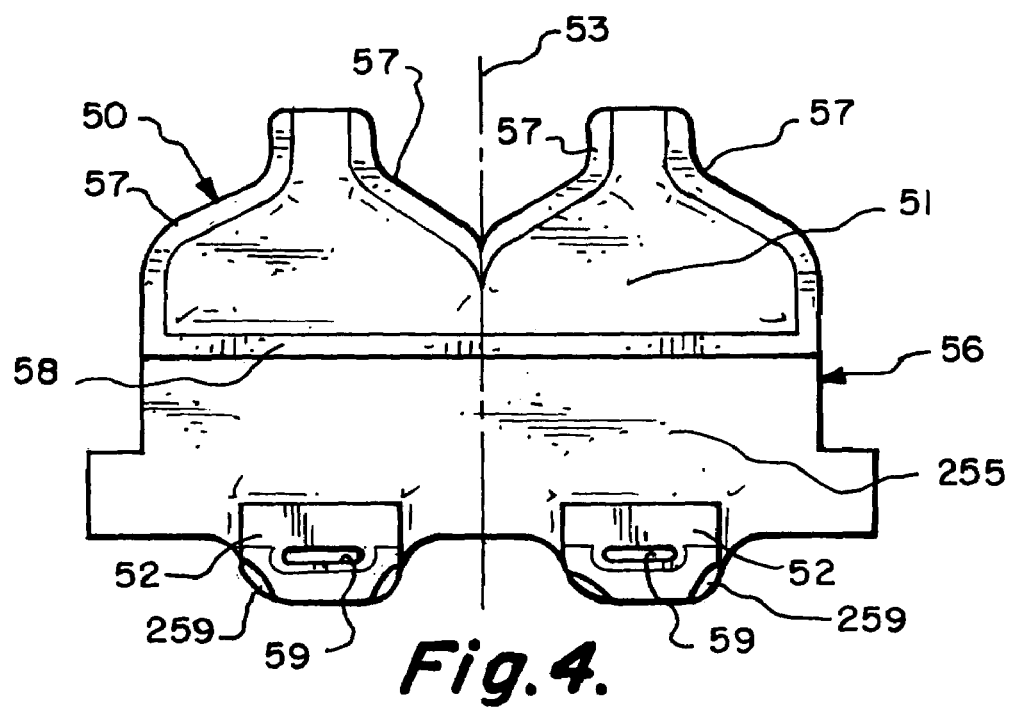
FIG. 4 is a plane view of FIG. 3 wherein the additional reinforcing material has been folded over and heat sealed to the main body to reinforce the body of the device of FIG. 1 in the regions indicated creating a form congruent to the form of FIG. 2.

FIG. 3 depicts an alternate construction, first piece 50 of the sheath body 2 described with reference to FIG. 2. It is cut from the same film material by any technique described above. It incorporates additional material which, when folded and heat sealed as described below, serves to reinforce areas of the sheath. This first piece 50 is symmetrical about the longitudinal centerline 53 and has a distal section 51 which is intended to be folded over the centerline 55 onto the distal portion of the body section 255. The first piece 50 also includes proximal tab sections 52 which are folded over the tab centerline 54 onto the proximal portion of body section 255. As can be seen in FIG. 4, the folded over tab sections, 52 and distal section 51 are heat sealed to body section 255 and reinforce it in the overlapped areas. Once the folded over sections are heat sealed to body section 255, the alternate construction has the same shape as the first piece 2 shown in FIG. 2.

Figure 39:
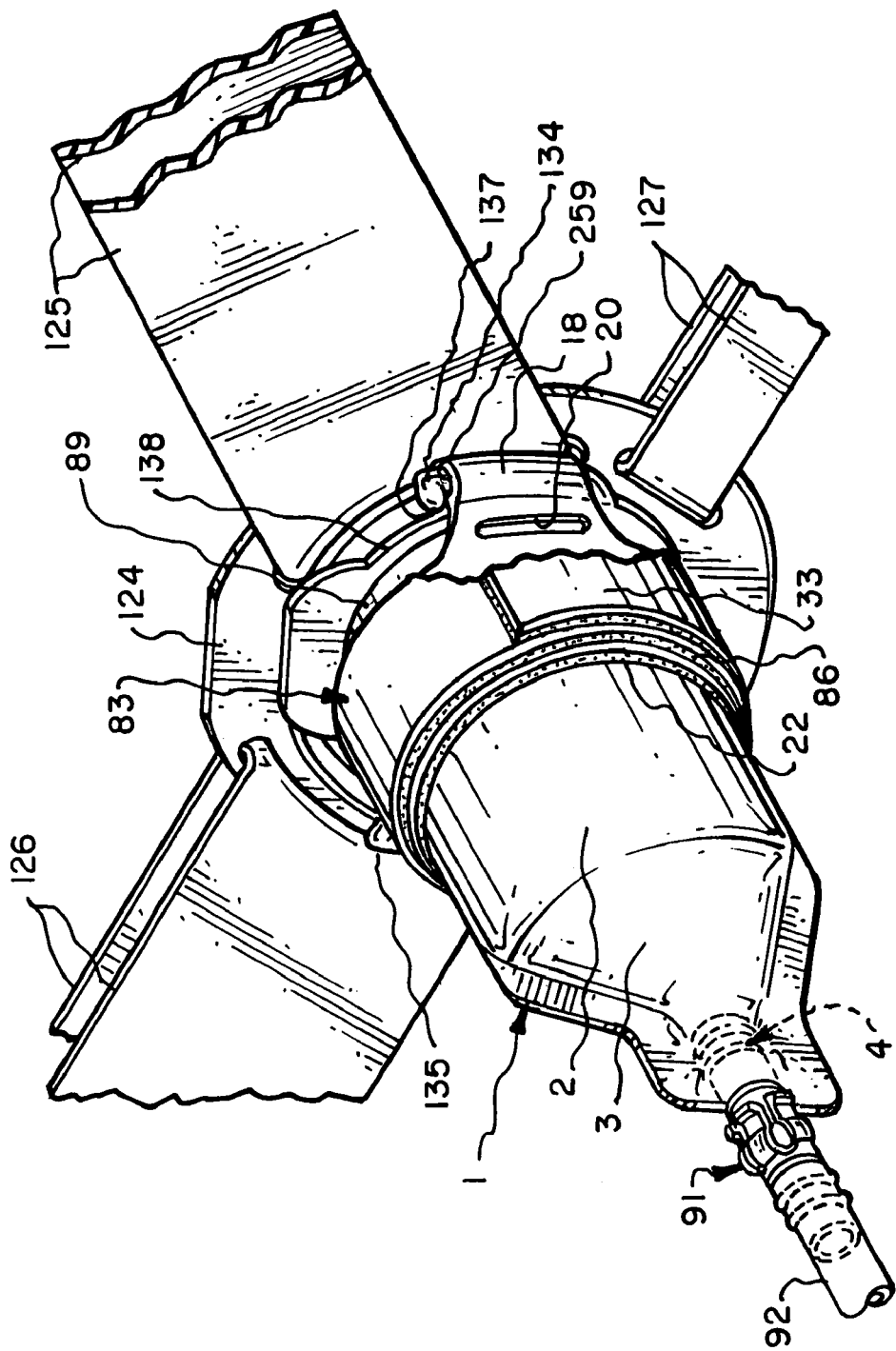
FIG. 39 is an isometric view of the device of FIG. 1 made from the reinforced sheath construction depicted in FIG. 4 attached directly to the face plate of FIG. 37 without the use of straps.

FIG. 4 depicts the second step of construction using the alternate first piece 50 wherein the folded over reinforcing sections of die cut film body have been heat sealed to the body section 255 forming a reinforced die cut film body 56. The folded over distal section 51 is heat sealed along its peripheral edge areas 57 and transverse areas 58. Tab sections 52 are heat sealed forming sealed areas 59, leaving the proximal portions 259 unsealed to form a loop in the tabs so that a sheath fabricated from this alternate construction 50 may be attached directly to a user worn faceplate retention ring as depicted in FIG. 39. Subsequent to this second stage of construction, the first piece of the alternate construction 50 is identical in its planer form to the first piece shown in FIG. 2 and differs only in that it has reinforced areas and loops in the tabs. The reinforced die cut film body 56 is intended for use in the event polymeric material is not available in a thickness sufficient to provide the physical properties for the sheath 1 to perform its intended functions or it is desirous to provide a sheath for patients having short penises.

Because of the congruence between the first piece 2 and the reinforced die cut film body 56, the remaining Figures and descriptions will only reference a sheath made from a first piece 2. It should be noted however, that the alternate reinforced die cut film body 56 as described with reference to FIG. 4, can be used interchangeably with the sheath first piece 2 without departing from the spirit or intent of the present invention.

Figure 5:
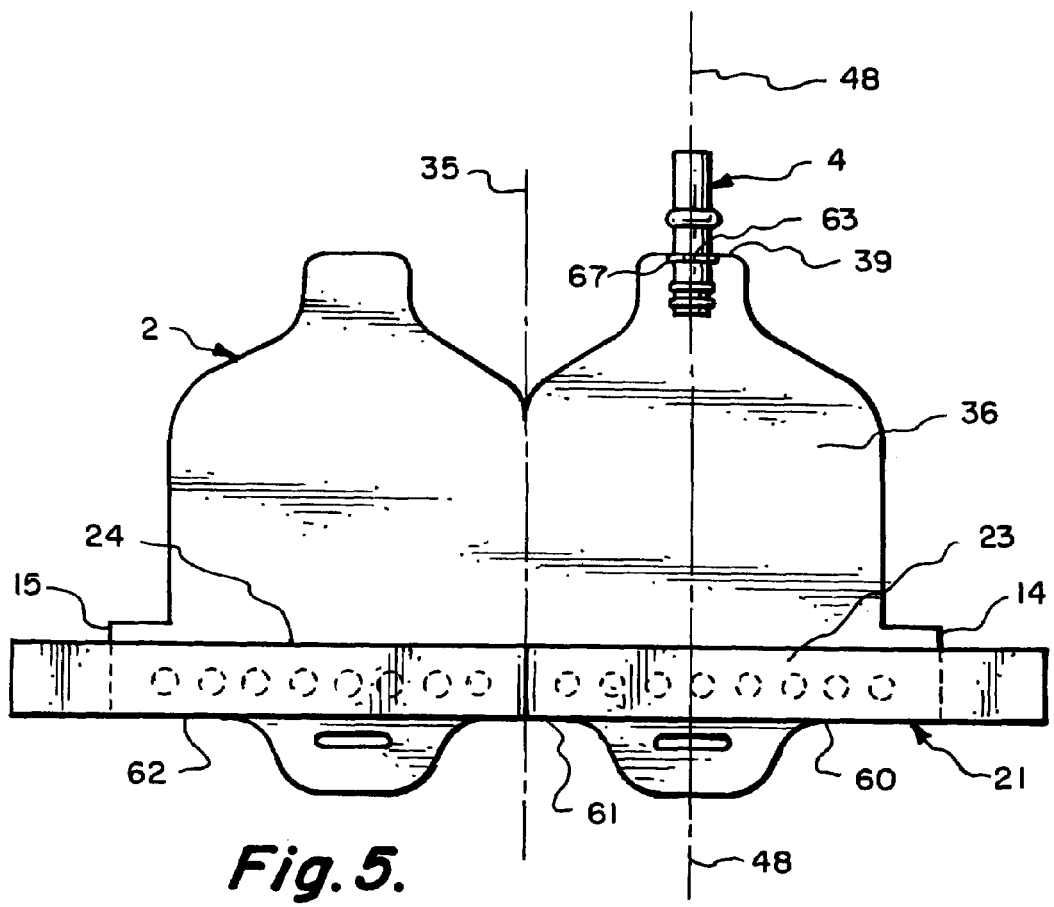
FIG. 5 is a plane view of a second stage in the fabrication of the sheath device of FIG. 1 wherein functional components are positioned on the cut form shown in FIG. 2 or FIG. 3.

FIG. 5 depicts a second stage of construction starting with the first piece of the sheath body 2 wherein a gel strip assembly 21 is mated (having had a release liner removed to expose an adhesive surface) to the interior surface of sheath body 2. The gel strip assembly 21 is centered on the body centerline 35 and coincident with the three proximal edges 60, 61, 62 of the sheath body 2 and adhesively bonded to sheath body 2 by the application of a uniform pressure applied to the entire surface of the two folded strips of a release liner film, right half 23 and left half 24, for a predetermined period of time. The adhesive is especially chosen to insure a permanent bond of the gel strip subassembly 21 to the polymeric material of sheath body 2. A more detailed description of the gel strip subassembly 21 is provided below with reference to FIGS. 7–9. A male coupling device 4 (more completely described below and shown in FIG. 6) is positioned on the centerline 48 of the interior of right side segment 36 of sheath body 2 so that the distal edge 63 of a heat sealing ring 67 is coincident with a distal edge 39 of the right side section 36. Male coupling device 4 is maintained in this location during assembly by appropriate jigs and fixtures, well known in the industry and not described herein, in preparation for the next step in the assembly of sheath 1 as is explained with reference to FIG. 10.

Figure 6:
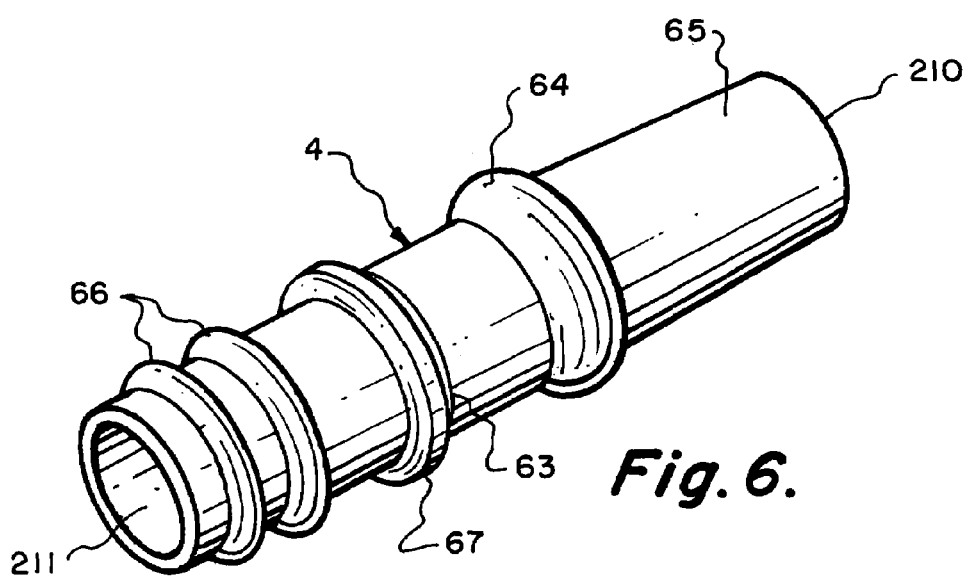
FIG. 6 is an isomeric view of a male coupling device for attachment to the device of FIG. 2 or FIG. 3.

FIG. 6 is an isometric view of male coupling device 4. It is molded from a suitable polymeric material having dimensional stability, resistance to the effects of exposure to urine and a melt index allowing it to be heat sealed to the thin polymeric material from which sheath body 2 is fabricated. The male coupling device 4 has a fluid entrance 211 and a fluid outlet 210. The coupling distal portion 65 has a smooth tapered surface which sealably mates with a female coupler 91 described with reference to FIG. 22. Proximal to the tapered coupling distal portion 65 is a rounded positioning boss 64 which, in conjunction with a mating feature 95 on the female coupler 91 of FIG. 22, helps to position the male coupling device 4 in a fluid tight relationship with the female coupler 91. At the proximal end of the male coupler are two closely spaced distal sealing rings 66 and a more distal sealing ring 67 having distal edge 63. The male coupling device 4 is heat sealed to sheath body 2 as more fully described with reference to FIG. 10.

FIG. 7 is an isometric view of a pre-application gel strip assembly 68. It differs from gel strip assembly 21 only in that gel strip assembly 21 has a release liner covering an adhesive surface which is removed to affix the gel strip 21 assembly to the sheath body 2, as is shown more fully in FIGS. 8–9. The gel strip assembly 68 consists of four components. The first two are lengths of polymeric release liners which have been folded over onto themselves comprising a patient contacting right release liner piece 23 and a shorter, right gel contact segment 69 and a patient contacting left release liner piece 24 and a shorter, left gel contact segment 70. Both the right and left gel contact segments 69, 70 are folded under the patient side segments and are perforated with a plurality of holes 71, 72 respectively. The area of the holes has been selected to permit the desired amount of surface area of the viscous gel to exude through the holes during application of the release liners. Although circular perforations are shown, openings having alternate geometry are acceptable providing the exposed area is equivalent. The release liners folded edges 73 and 74 are coincident and aligned with the centerline 75 of gel strip assembly 68. The third component is a viscous polymeric gel 22, preferably a conformable, soft, flexible, extensible, biologically inert, gel material possessing long term physical and chemical stability, with a thickness in the range of 0.05–0.10 inches. The polymeric gel 22 should not absorb, swell, erode or be permeable to urine. The polymeric gel 22 is intended to seal to the penile shaft and stretch with the penile tissue as the penis changes in diameter without loosing adhesion or its integrity, without allowing leakage. Accordingly, it has a relatively high modulus of elongation and high shear strength. While the polymeric gel 22 must adhere to penile tissue it should not adhere so aggressively that it cannot be readily removed or, when purposely removed, leave a residue (or an unacceptable or not easily removed residue) on the tissue. A specially formulated, 2-component silicone mixture which can be fully cured in a short period of time is preferred as the material of choice for the polymeric gel 22. The fourth component is a double backed adhesive strip 25. One release liner (not shown) is removed prior to the adhesive strip being mated to the polymeric gel strip 22 in the process of forming and curing the gel strip 22 from its component parts in a production process not described herein. The widths of the left and right side release liner segments 23, 24, the polymeric gel 22 and the double backed adhesive strip 25 are equal.

The plurality of perforations 71, 72 in the gel contact segments 69, 70 allow portions of the viscous gel strip 22 to be extruded through the thin film of the contact segments 69 and 70 so that the gel releasably bonds to the undersides of the longer segments 23 and 24 thus effectively releasably bonding the layers of the folded release liners together. This bonding prevents unwanted, premature separation of the layers of release film which could otherwise interfere with insertion of the penis into the sheath. Portions of the longer right and left side release liners 23, 24, identified as release liner segments 28 and 29 respectively, extend beyond the edges of gel strip 22 and the right and left gel contact segments 69 and 70. These segments are further described with reference to FIG. 10.

FIG. 8 is an enlarged, cross-sectional view taken along line 8—8 of FIG. 7. The right side release liner 23 and left side liner 24 are positioned with their folded edges 73 and 74 coincident with the centerline 75 of the polymeric gel strip assembly 68. Bonded to the underside and coextensive with polymeric gel strip 22 during its production, as noted above, is a double-backed adhesive strip 25. The double-backed adhesive strip consists of four components. The first component is a first adhesive layer 76 coextensive with the gel strip. The adhesive 76 has been chosen especially to form a permanent bond with the polymeric gel 22. The second is a thin (0.01 inches or less) polymeric carrier film 77 onto which the adhesive 76 has been applied. The third is a second adhesive layer 78, coextensive with the carrier film 77, particularly suited to establish a permanent bond with the polymeric film material of the sheath body 2 so as to effect permanent attachment of the polymeric gel 22 to sheath body 2. The fourth is a release liner 79, which completely covers the second adhesive layer 78 until the gel strip assembly 21 is ready to be affixed to sheath body 2, following removal of the release liner 79.

The double-backed adhesive strip 25 is a necessary component of the sheath 1 of the invention, carefully chosen to mate the polymeric gel 22 to the polymeric film of sheath body 2 as the properties of the polymeric film and the polymeric gel 22 are such, that while each has the unique characteristics that make them desirable for their independent functions, these same properties prohibit them from permanently bonding to each other to provide a reliable barrier preventing fluid leakage from the interior of the sheath 1.

FIG. 9 is an isometric view of the pre-application gel strip assembly 68 from which the release liner 79 is being peeled away to create gel strip assembly 21. Release liner 79 is removed just prior to the mating of gel strip assembly 21 to sheath body 2 as illustrated in FIGS. 1 and 5 where the assembled component is identified as gel strip 21 following removal of the release liner and placement onto the sheath body 2.

Figure 10:
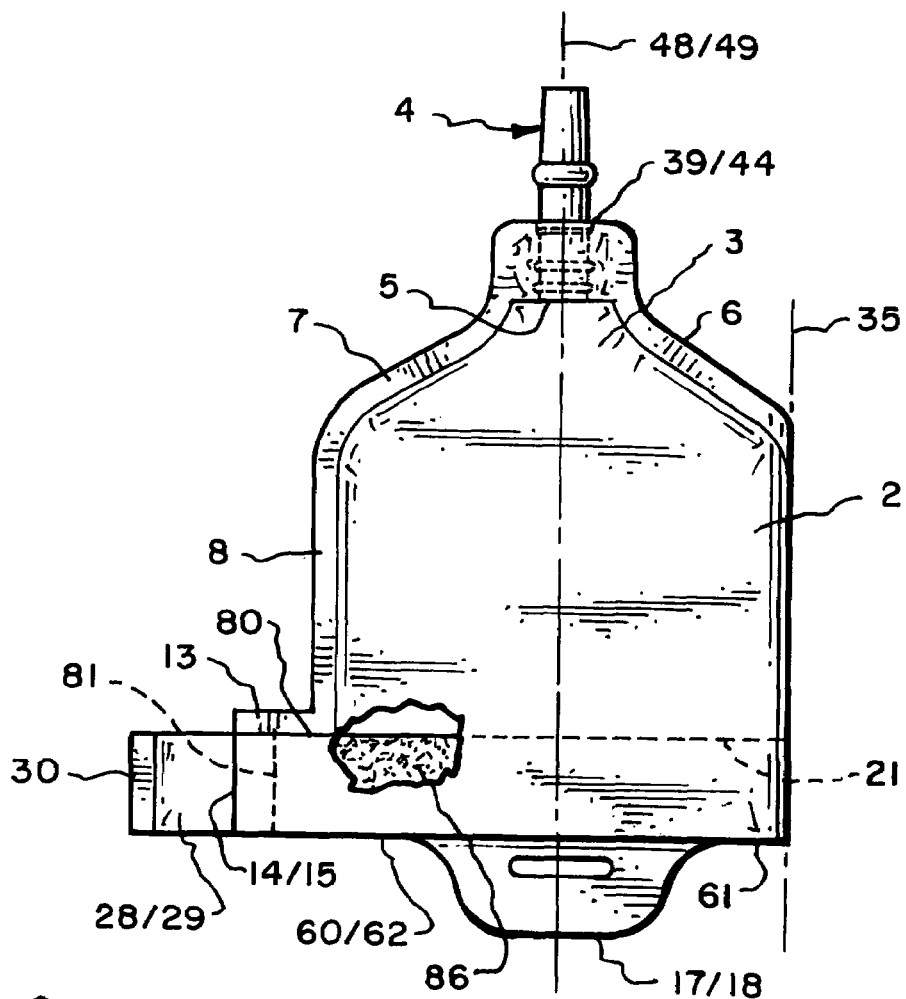
FIG. 10 is a plane view of a third stage in the fabrication of the device of FIG. 1 partially cutaway to show hidden features.
Figure 15:
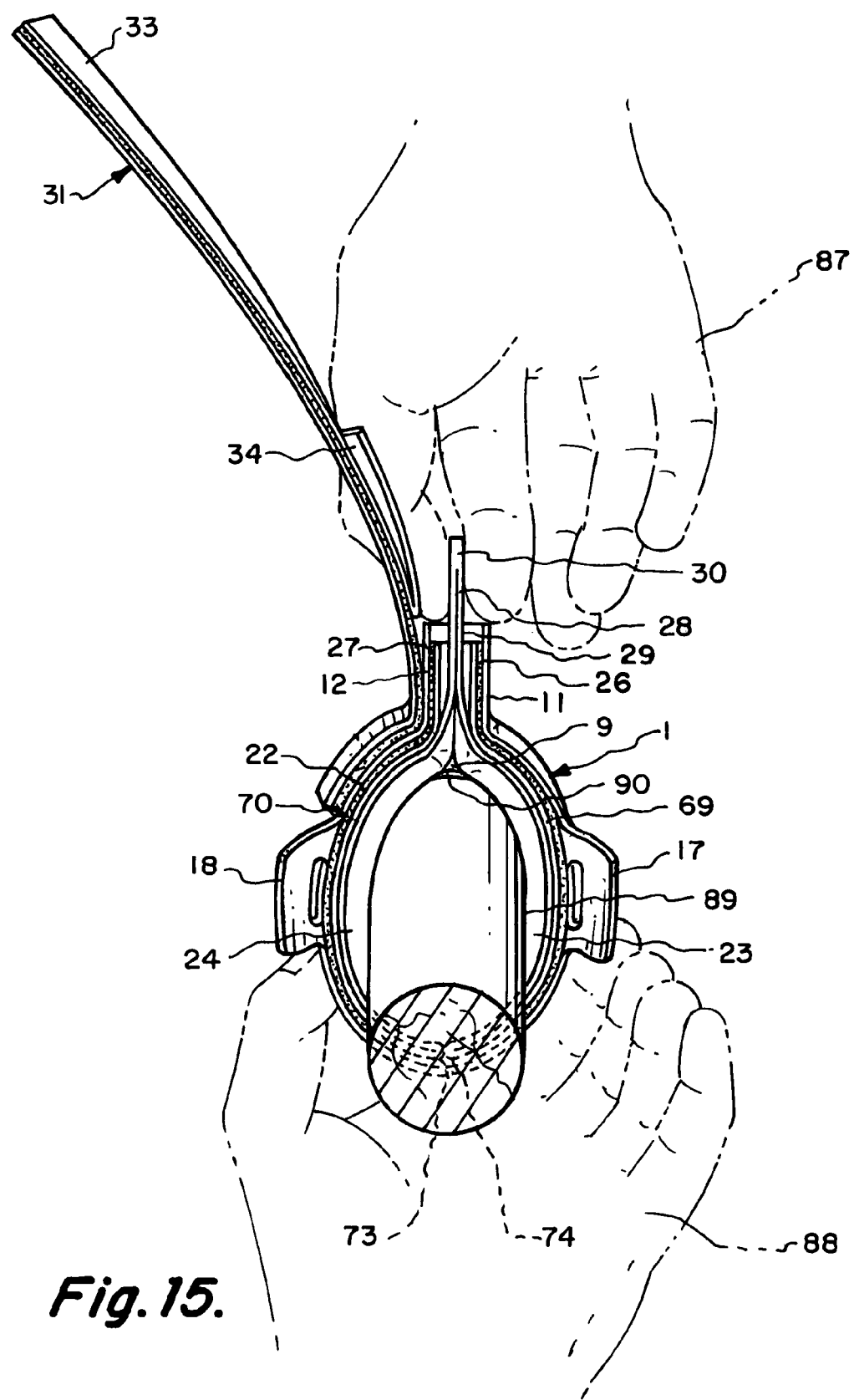
FIG. 15 is a view from the patient's perspective wherein the patient is pressing the device of FIG. 1 against the underside of his penis and grasping the release liners of the gel strip assembly in preparation for their removal.
Figure 16:
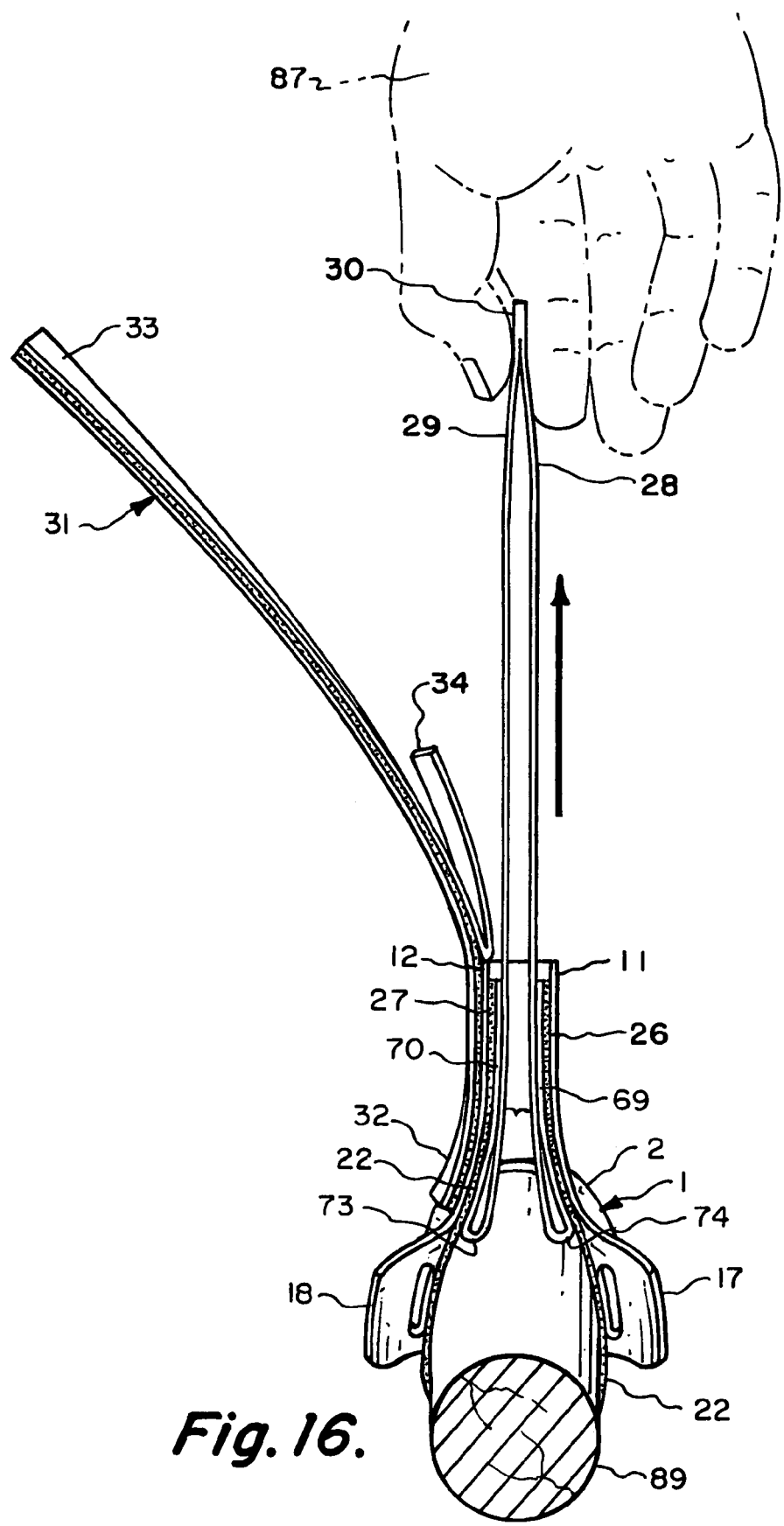
FIG. 16 is a view from the patient's perspective wherein the patient is grasping and removing the release liners of the gel strip assembly from the gel strip assembly.

FIG. 10 is a plan view of the third stage of construction of the sheath body 2, wherein the right side 36 and the left side 37 of the sheath body 2 (Reference FIG. 2) have been folded flat about the centerline 35 so that all perimeter edges are aligned and, with the exception of the tabs 17, 18 and specified edges 14, 15, 60, 62, 61 of sheath body 2, the edges are heat sealed to a minimum width of 0.10 inches so that the heat sealed areas 5, 6, 7, 8, 13 form a fluid tight continuous seal around the perimeter of sheath body 2. The male coupling 4 is heat sealed about its circumference at the distal end of the funnel area 3, proximal to edges 39, 44 thereof. Polymeric gel strip assembly 21 is also folded over in the interior of sheath body 2 and bonded to it by the adhesive 86 which is coextensive with the underside of polymeric gel 22. Gel strip assembly 21 is coincident with the inner edge 80 of the heat sealed area 13. The top edge 81 of the polymeric gel 22 is located at a distance of about 0.15 inches from edges 14, 15 of tabs 11, 12. The outermost ends of the release liner segments 28, 29 are joined together to form a tab 30, at their ends, preferably by means of heat sealing, during this assembly step. Joining the ends together insures that as the release liners are removed, as will be subsequently described, they will be removed from the right side and the left sides of the polymeric gel strip simultaneously starting at the centerline 35 where the adjacent folded edges are positioned at the lowermost point of the penis of the user. Removing the release liners in this manner insures a continuous, gap free, and fluid tight releasable bond between the polymeric gel 22 and the circumference of the penis. FIGS. 15 and 16 further illustrate the removal of the release liners from the gel strip. To aid in placement of the sheath the internal diameter of the sheath is made larger than the diameters of the $90^{th}$ percentile patient and of sufficient length to fit over the head of the penis of this same population group.

Figure 11:
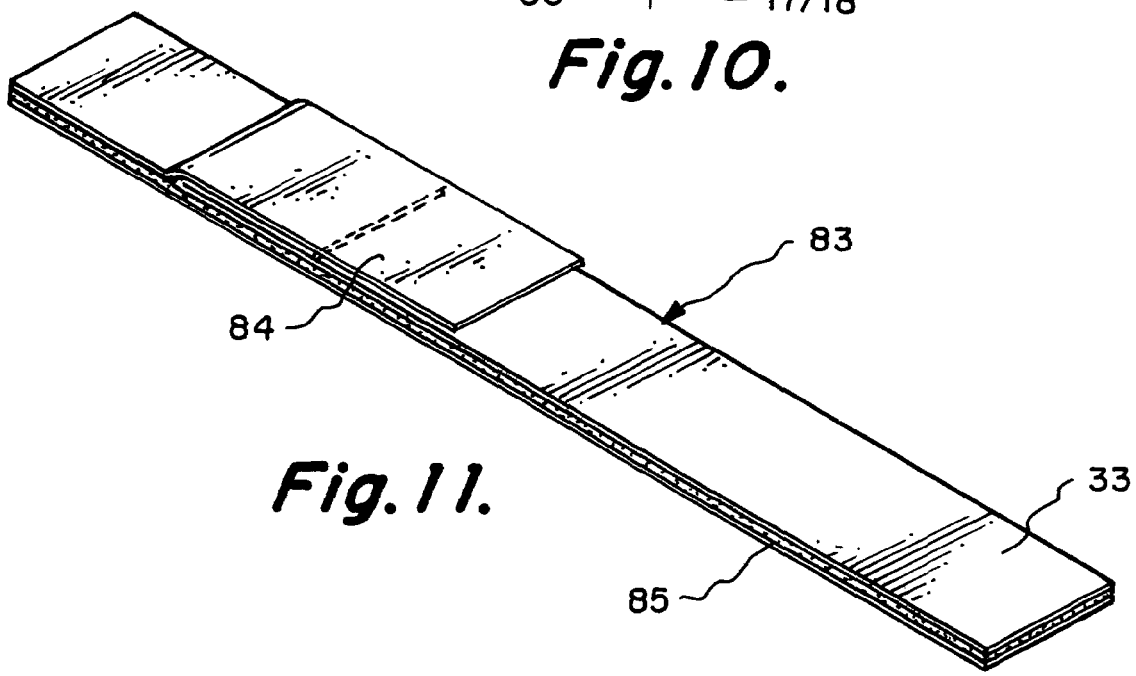
FIG. 11 is an isometric view of an elastomeric adhesive backed tape strip prior to its application to the sheath of FIG. 10.

FIG. 11 is an isometric view of an elastic adhesive tape assembly 83. It is fabricated from a thin, polymeric, base material 85 preferably having an elastic modulus in excess of 100% so that it may be stretched to provide tension throughout its period of use. It is coated with a high tack adhesive formulated to securely adhere to the tape base material 85 and to the polymeric film from which sheath body 2 is fabricated. The specially selected adhesive has properties which include the ability to maintain a secure bond while under tension as a result of the tape strip being stretched around the sheath to compress and secure the sheath to the penis of the user and also be easily strippable by the user when the sheath 1 is to be removed after use. The adhesive tape assembly 83 is provided with two release liner segments, a short segment 84 and a longer segment 33, which includes the tab segment 34 (shown in FIG. 12) that remains in place until the tape is to be affixed to the surface of sheath. In the assembly depicted in FIG. 11, release liner segment 84 covers approximately one inch of adhesive and extends over the longer release liner segment for approximately 1.75 inches making the segment easy to remove in preparation for attaching the tape assembly to the sheath as shown in FIGS. 1 and 13 wherein it is identified as tape strip assembly 31 as explained in reference to FIG. 12.

Figure 12:
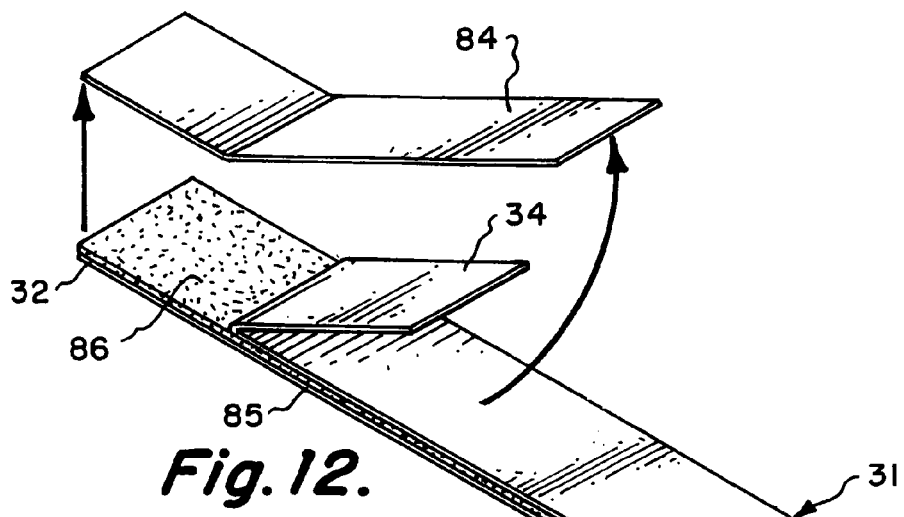
FIG. 12 is an isometric view of the elastomeric adhesive backed tape strip of FIG. 11 with a portion of the adhesive exposed prior to application to the sheath of FIG. 10.

FIG. 12 depicts a tape strip assembly 31 which differs from the tape strip assembly 83 in that the release liner segment 84 has been removed to expose approximately 1.0 inch of the adhesive 86 which covers the elastomeric base material 85. Removal of the release liner segment 84 exposes the previously covered tab 34 of the release liner 33. The tape release liner segment 34 is shown in an elevated position for clarity. It would normally be approximately parallel to the surface of the tape assembly. Tab 34 is subsequently grasped by the user and peeled from the adhesive coated tape strip 85 as the user prepares to secure the sheath to his penis as is described and illustrated in FIGS. 18, 19 and 20.

Figure 13:
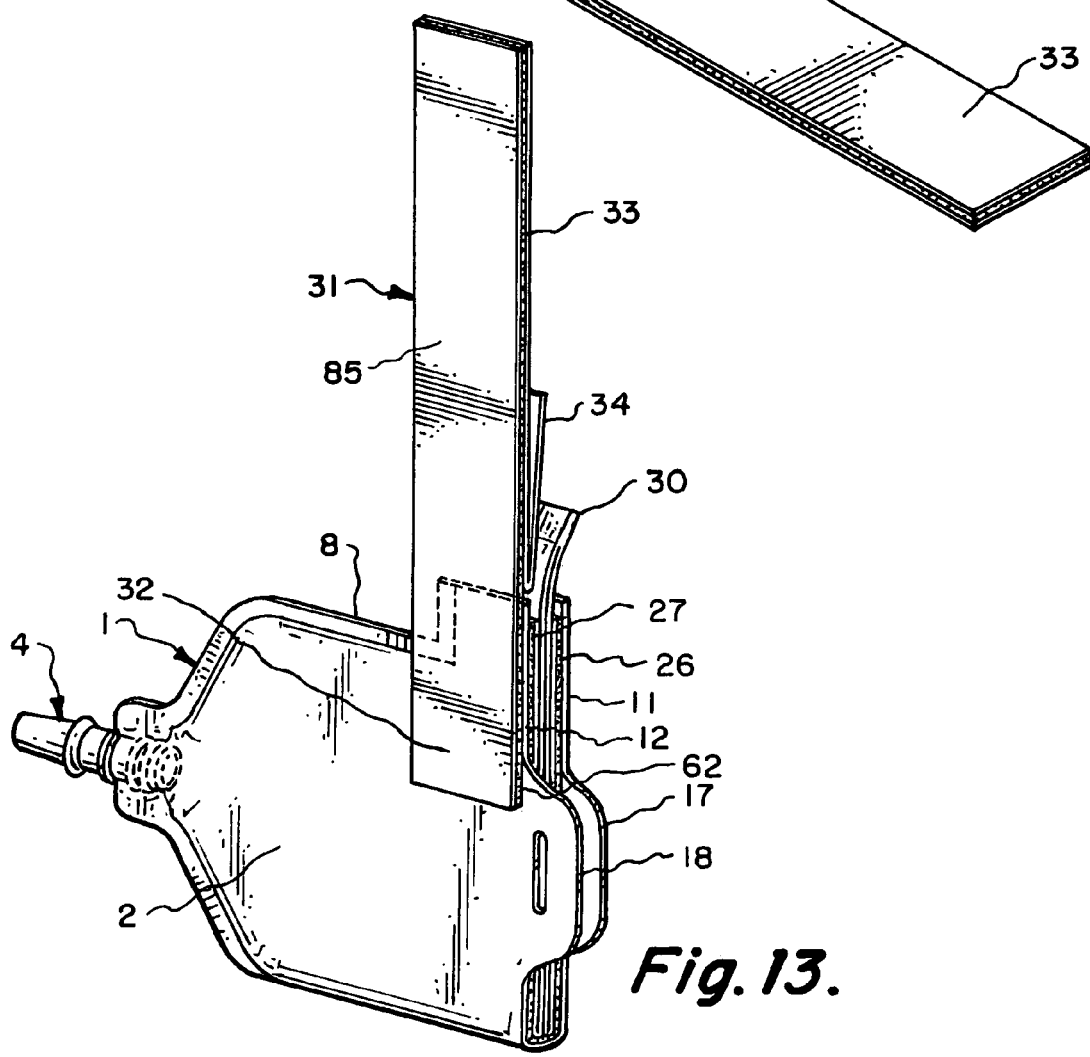
FIG. 13 is an isometric view of the tape strip identified in FIG. 12 following removal of one segment of release liner and application of the tape strip to the sheath of FIG. 10.

Reference to FIG. 13 illustrates the fourth and final step of assembly for a sheath 1 incorporating features of the invention. The tape strip assembly 31 is applied to the outer surface of the sheath body 2 following the removal of the release liner segment 84. The tape strip assembly 31 is placed so that it is coincident with edge 62 and affixed to sheath 2 so that the upper edge of the adhesive exposed on the inner surface of the lower tape segment 32 by the removal of release liner segment 84 is approximately collinear with the outer edge of the heat sealed edge area 8. It should be noted that the folded edge of tab 34 is in practice, also collinear with the outer edge of heat sealed edge area 8, however it is shown above the flap ends 11, 12 for clarity. It should be also be noted that tape strip 31 is wider than the flaps 11, 12 of the sheath body 2. This is to insure that as the adhesive coated base tape material 85 is wrapped around the sheath body 2 to create a snug fit around the penis of the user, as shown in FIGS. 18 to 21, a smooth, sealed edge is provided so that the sheath will not be snagged on the users clothing and the additional seal provided by the overlap, further insures the fluid tight seal in this area.

Figure 14:
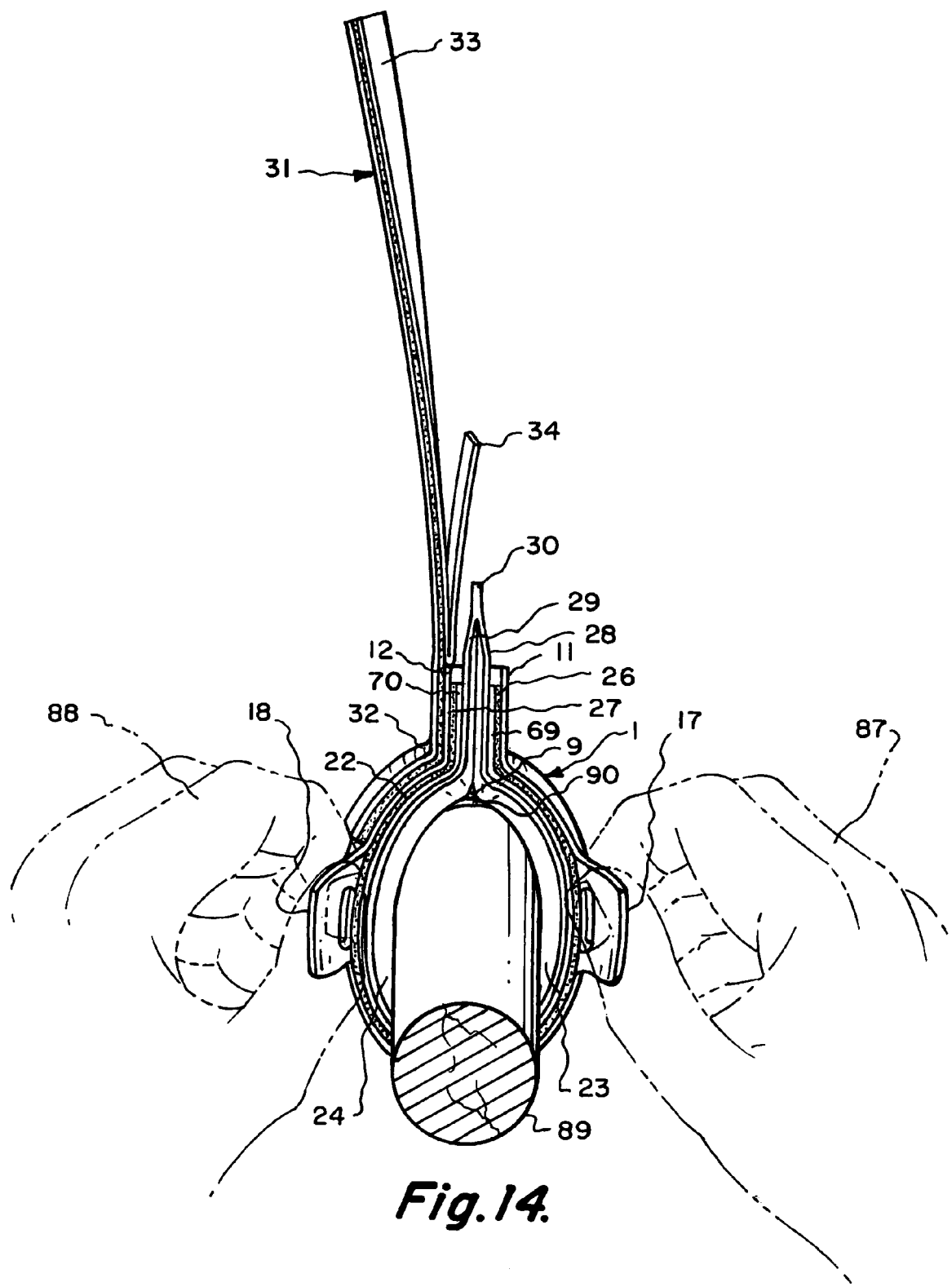
FIG. 14 is a view from the patient's perspective wherein the device of FIG. 1 is being applied to the user's penis.

Reference to FIG. 14 illustrates, as viewed from the perspective of the user, the method whereby the user of the sheath device 1 inserts his downwardly extending penis 89 into the proximal opening 9 of sheath body 2. To facilitate insertion, a right handed user would typically grasp the right sheath tab 17 with his right hand 87 and left sheath tab 18 with his left hand 88 and pull the sheath body 2 over the shaft of his penis towards his body so that, as a minimum, his penis is inserted into the sheath body 2 a sufficient distance to insure that the glans 90 of his penis is distal to the patient right and left release liners 23, 24 respectively which cover the polymeric gel 22. In the event the sheath 1 was being placed on the patient by a caregiver instead of by the user himself, the position of the hands would be reversed as the caregiver would typically be facing the patient.

FIG. 15 depicts a right handed user removing the right and left side release liners 23, 24 covering the polymeric gel strip 22 after positioning his penis 89 in sheath body 2. The user first pushes the sheath upwards so it is pressed to the underside of the penile shaft. He then grasps the heat sealed tab 30 joining the two upper patient side folded release liner film segments 28, 29 together and pulls them vertically in a direction away from the longitudinal axis of the sheath body 2 to expose the polymeric gel strip 22 after the liners are completely removed from sheath body 2. As tab 30 is pulled, both patient side release liner segments 23 and 24 are simultaneously pulled up in relation to the polymeric gel strip 22. As the release liner tab 30 is pulled away from the longitudinal axis of sheath body 2, the right and left gel side release liners 69, 70 are peeled away from the surface of the polymeric gel strip 22 as the patient side liners transition into gel side liners at the folded edges 73 and 74 as shown in FIG. 8. The gel strip side release liners are effect "rolled" up over the surface as pulling on tab 30 continues until the release liners are clear of the sheath body 2. As the release liners are removed, they exert an upwards reactive force on sheath 2 surrounding the penis due to the resistance (peel strength) of gel adhesive forces opposing the peeling of the strips away from the surface of the gel. This upward pull on the sheath insures that the gel strip is releasably mated with the user's penis in a controlled manner as contact and adhesion of the gel strip to the penis is initiated at the lowermost portion on the circumference of the penis.

As can be seen in FIG. 16, while holding onto his penis with his left hand (not shown) the continued pulling upward on patient side release liner segments 28, 29 results in completely peeling the gel strip side release liners 69, 70 from the surfaces of the upper right hand and left hand segments 26 and 27 respectively of polymeric gel strip 22 so it is completely exposed to and adhered to the circumference of the penis in both a clockwise and counter clockwise direction at essentially the same rate and in a continuous manner to preclude gaps in which no gel contacts the external surface of the penis.

Figure 17:
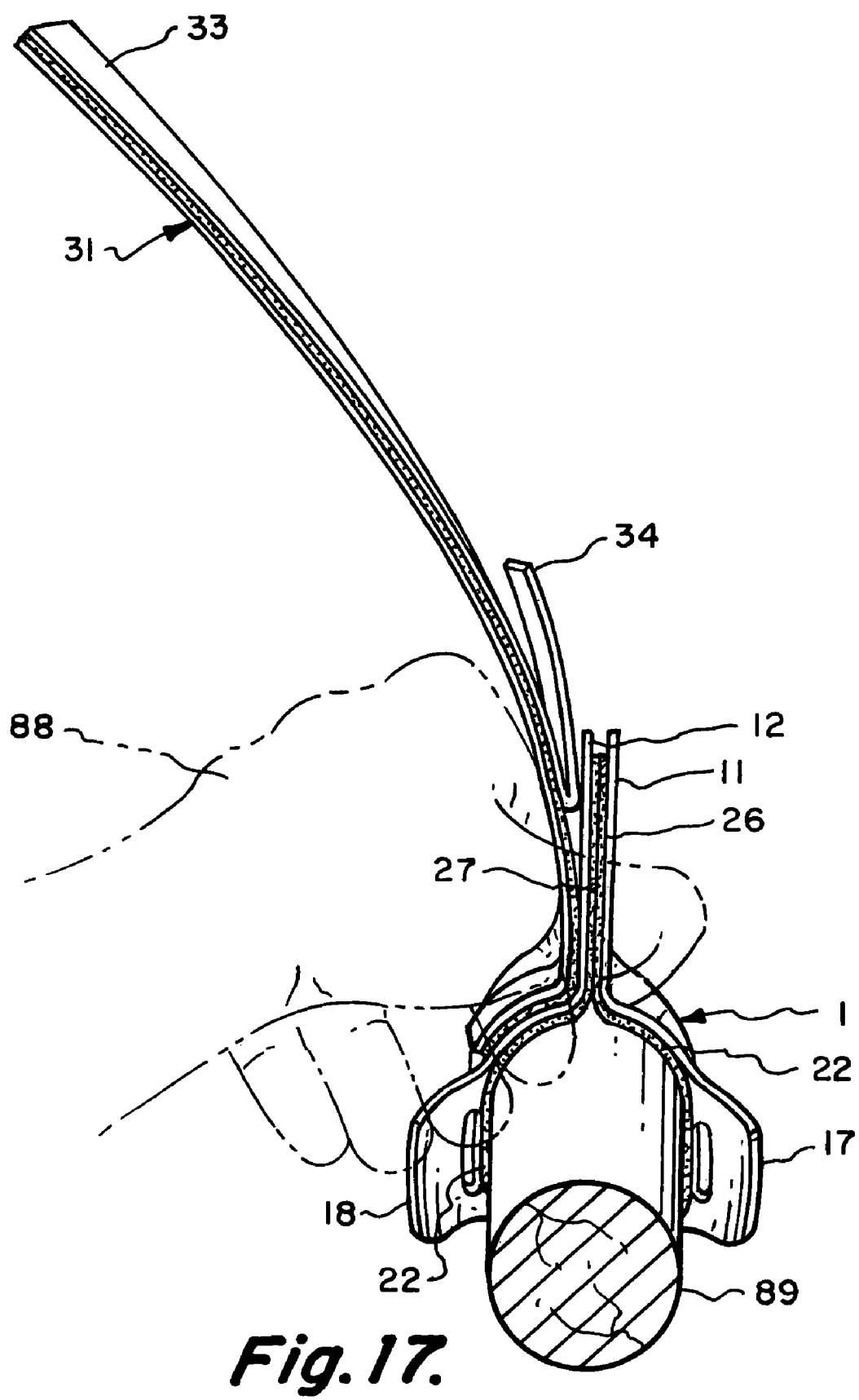
FIG. 17 is a view from the patient's perspective wherein the patient is pressing the exposed and opposing surfaces of the gel strip together to form a fluid tight seal around the user's penis.
Figure 18:
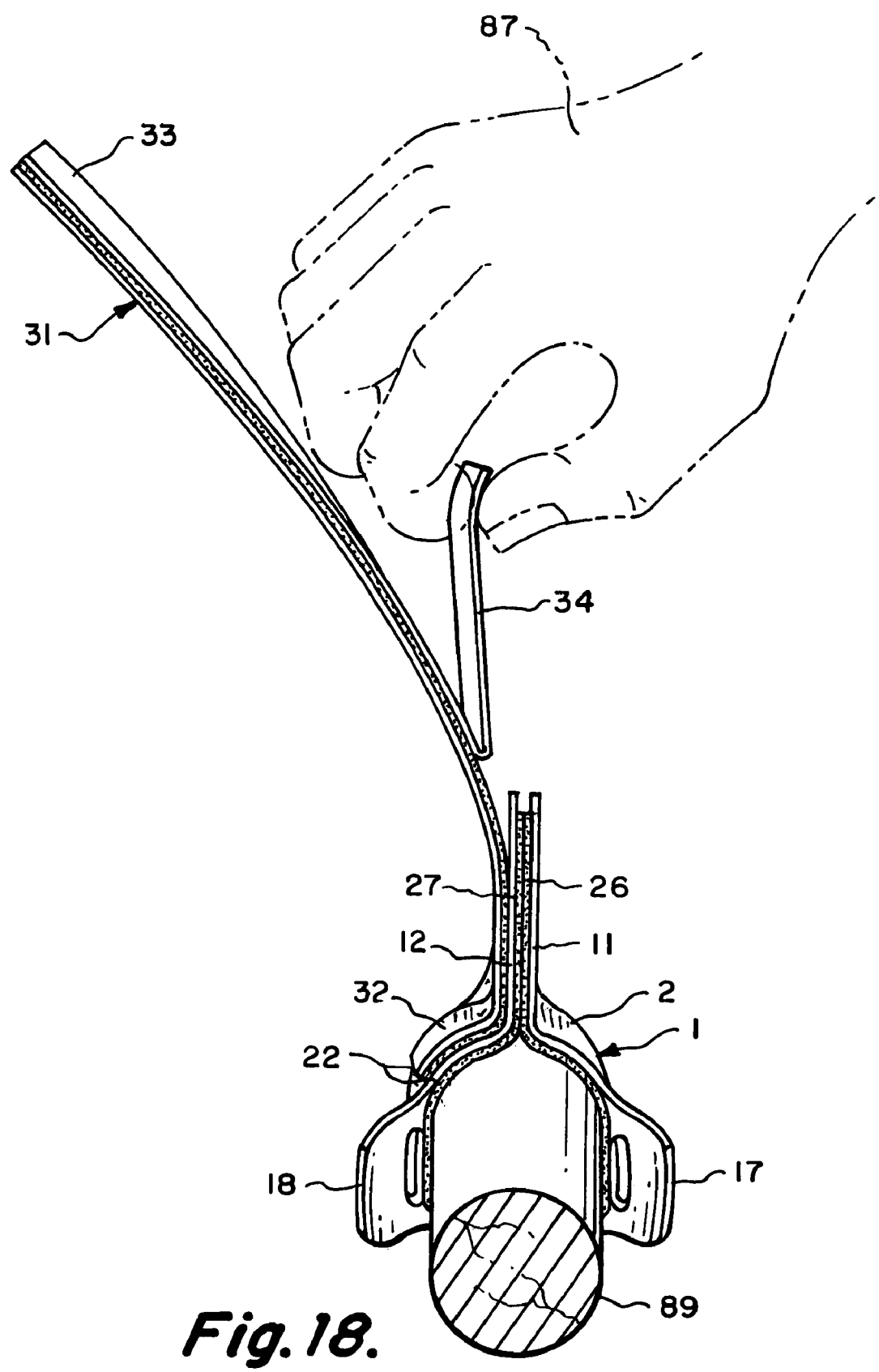
FIG. 18 is a view from the patient's perspective wherein the patient is removing the second release liner from the tape strip of FIG. 13 and exposing the remaining adhesive backing on the tape.

Following removal of the two release liners covering the inner surface of the polymeric gel strip 22, as described with reference to FIG. 16, the user gently presses on the outer surface of the sheath, starting at the underside and continuing around the entire circumference of the sheath to further insure gel strip contact and a fluid tight seal with the skin of the penis 89. Following this, the user squeezes the right flap and left flap 11, 12 of the sheath body 2 together as depicted in FIG. 17. As the sheath flaps 11, 12 are squeezed together, so are the vertical ends of the upper right hand segment 26 and left hand segment 27 of polymeric gel strip 22 extending upwards from the portion of gel strip 22 surrounding the penile shaft. Pressing the gel strip end segments together creates a fluid-tight seal between them extending down to and around the circumference of the penis. The interior of sheath 1 is now completely sealed around the penis. Fluid outlet 10 of male coupling 4, as intended, provides the only outlet from the sheath of the present invention through which urine can flow.

Referring to FIG. 18, viewed once again from the perspective of the user, the removable release liner 33 of the adhesive backed tape strip assembly 31 is shown being removed by the right hand 87 pulling on release liner tab 34 in preparation to securing the sheath body 2 to the penis 89 of the user while the gel strip segments 26 and 27 affixed to sheath tabs 11 and 12 remain sealed together.

Figure 19:
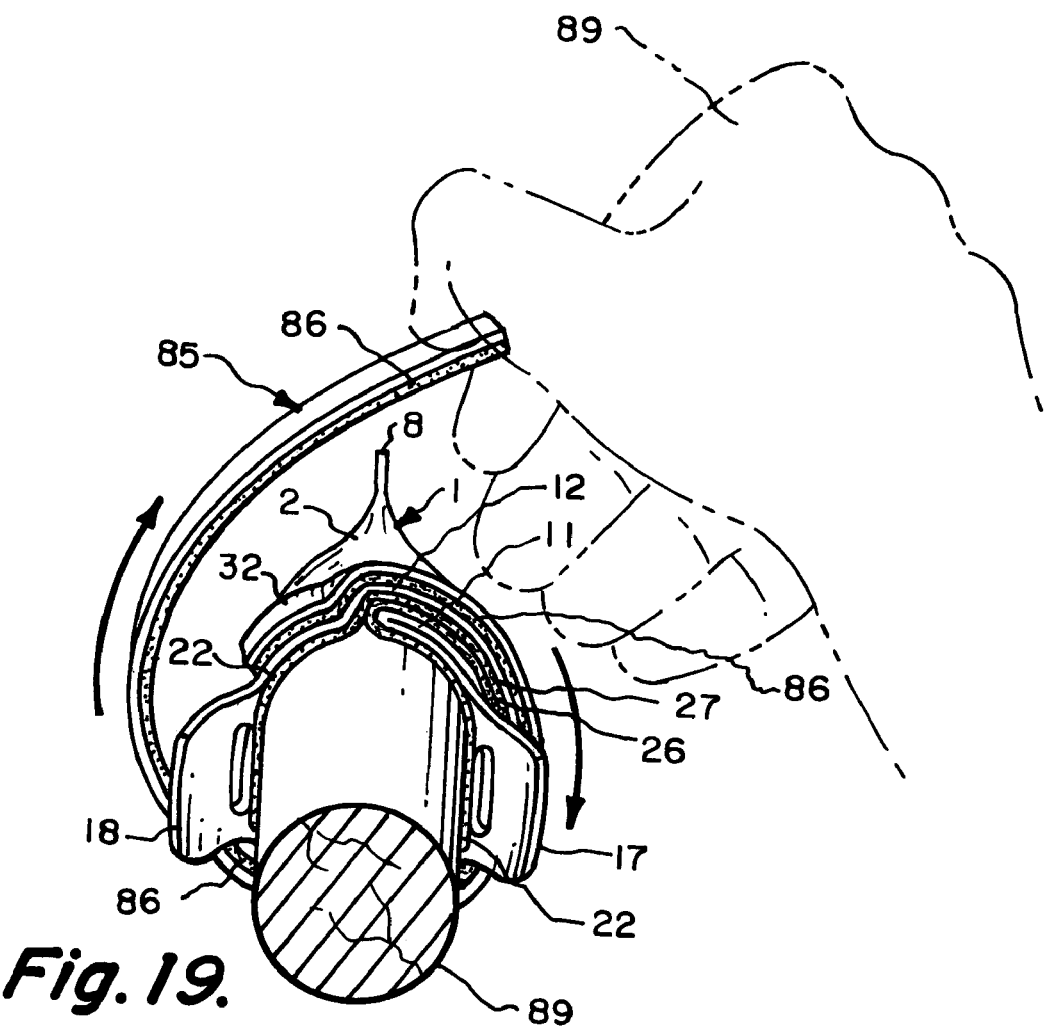
FIG. 19 is a view from the patient's perspective wherein the patient is stretching and wrapping the adhesive backed tape around the circumference of the device shown in FIG. 1 to secure the device to the penis of the patient.
Figure 20:
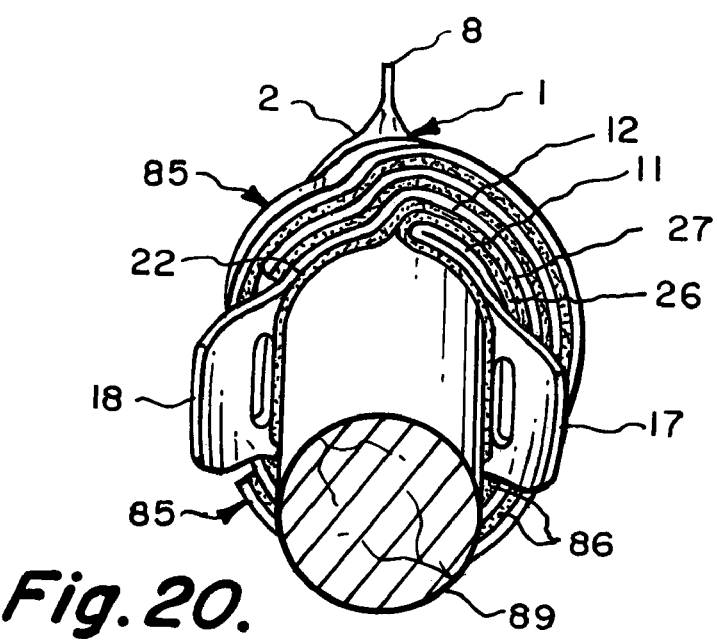
FIG. 20 is a view from the patient's perspective after securing the adhesive backed tape around the circumference of the device of FIG. 1.

Once the final tape release liner 33 has been removed from the tape strip assembly 31, the adhesive backed elastomeric tape strip 85 is stretched over the sheath flaps 11, 12, folding them together and down onto the outer surface of the sheath body 2 as shown in FIG. 19. The elastomeric tape is adhesively bonded to the outer surface of the sheath 2 by stretching the tape strip, folding any excess sheath material around the outer surface of the sheath and pressing the adhesive onto the outer surface of the sheath to create a snug fit on the penis. As noted above with reference to FIG. 1, the elastomeric tape is wider than the sheath tabs 17, 18 so that after the tape is wrapped around the sheath body 2, as illustrated in FIG. 20, a smooth exterior surface is obtained.

Figure 21:
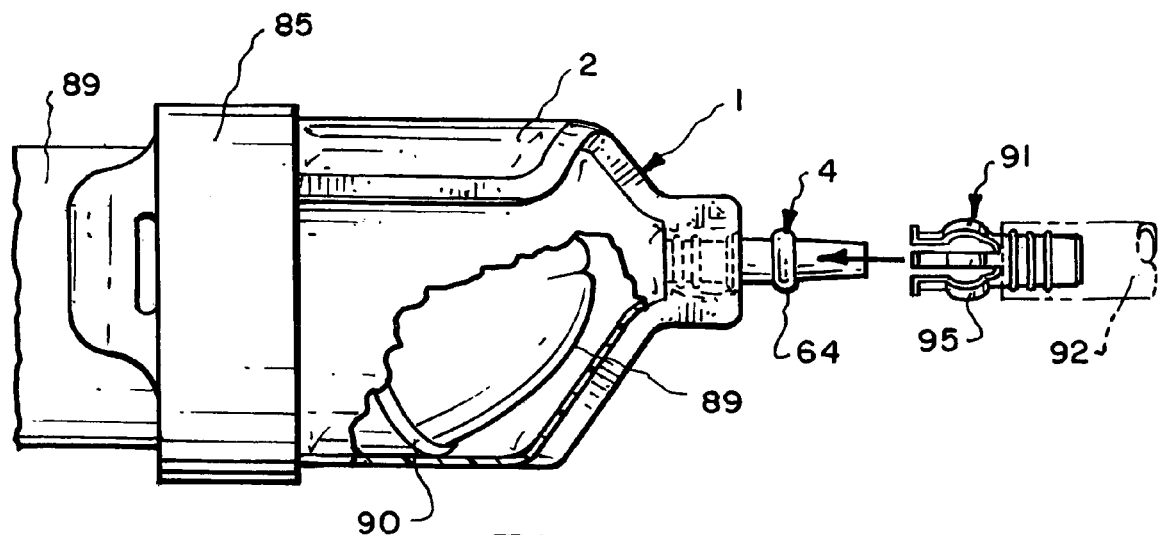
FIG. 21 is a side view of the device of FIG. 1 secured to the penis of the patient.

FIG. 21 is a lateral view of the user's penis 89 positioned properly within the sheath 1 so that the glans 90 is distal to the polymeric gel strip 22 (not shown as it is hidden below tape) with elastomeric tape strip 85 wrapped around the circumference of sheath body 2. Aligned with male coupling 4, is female coupler 91 connected to a length of fluid transport tubing 92. The female coupling and tubing will subsequently be described in greater detail.

Figure 22:
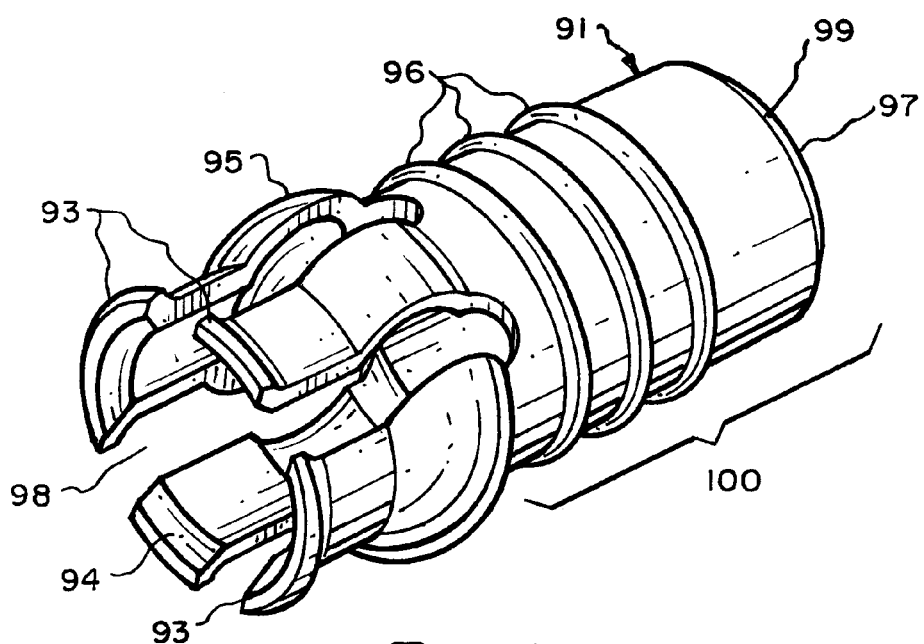
FIG. 22 is an isometric view of a female coupler which sealably mates with the male coupling device of FIG. 6.

Depicted in FIG. 22 is a female coupler 91 intended to be used in cooperation with male coupling 4 to allow for easily transferring a patient or user's urine from the sheath device 1 to a receptacle for temporary storage prior to disposing of the urine. The female coupler 91 is molded from a suitable polymeric material having dimensional stability and resistance to the effects of prolonged exposure to urine. Preferably it is molded from the same material as the male coupling 4 so that their coefficients of thermal expansion are matched to help insure a fluid tight fit when mated to each other. The female coupler 91 is designed to easily and securely sealably mate in a releasable manner with male coupling 4. To facilitate mating and sealing, the female coupler entrance 98 is provided with a plurality of outwardly tapered tangs 93 with a lead-in angle 94 of between 30 and 45 degrees. Distal to the opening 98 is a mating feature having an internally concave positioning boss 95 which encourages a corresponding convex positioning boss 64 on the male coupler 4 to seat within it. The bosses 64, 95 have a geometrical relationship such that the male boss 64 must be inserted to a sufficient depth within the coupler to affect a fluid tight seal between the external tapered portion 65 of male coupler 4 and the matching internal taper of the distal portion 100 of the female coupler 91 before the convex and concave bosses align. The proximal ends of tangs 93 form a circular opening that is smaller in diameter than the positioning boss of the male connector and require a force to connect the two components and also to disconnect them. The tangs act as cantilever beams in that they are flexed open as the positioning boss of male couple 4 is pressed into position. The design of the tangs is such that it is easier to affect a connection between the components than is to separate them. The axial force to separate the connectors is about two pounds. As a result of this design, the user is assured of a secure connect until he intends to disconnect the components. This design is superior to the current methods of connecting male condoms or sheaths which utilize barbed fittings, procured by the users as accessories, to connect to transfer or storage means. Fluid exits the female coupler through distal opening 99. The distal end of the female coupler has a taper 97 on it to facilitate attachment to a transfer or storage device. A plurality of sealing rings 96 help to maintain a secure connection to a tube 92 as shown in FIG. 21 or a storage or urine collection device described herein below.

Figure 23:
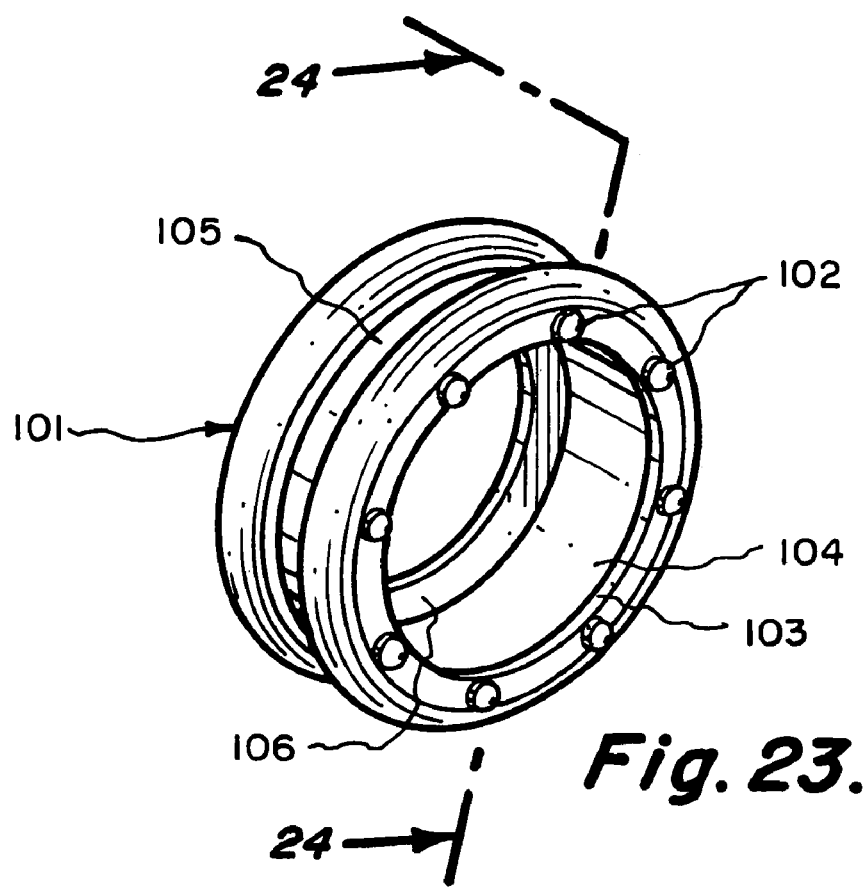
FIG. 23 is an isometric view of an optional locking ring for securing the mating of the female coupler of FIG. 22 to the male coupling device of FIG. 6.
Figure 24:
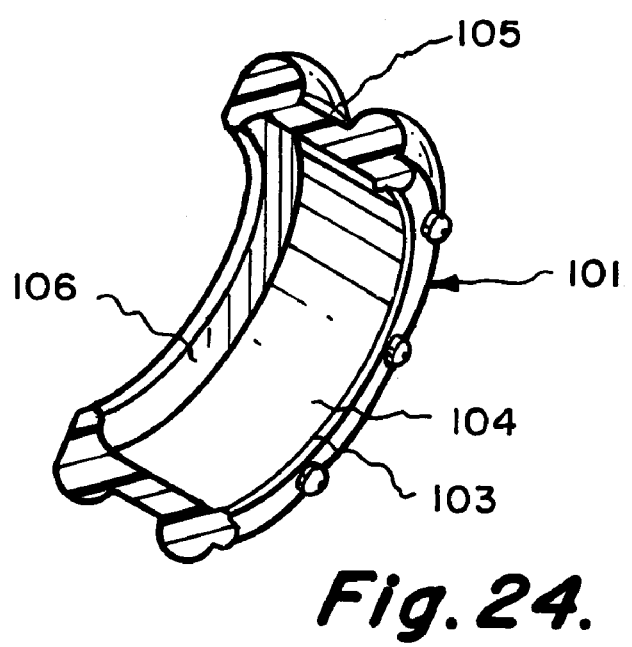
FIG. 24 is an isometric cross-sectional view of the locking ring of FIG. 23 taken along line 24—24 of FIG. 23.

As described in regard to FIG. 22, female coupler 91 is releasably mated with male coupler 4 and requires an axial force to affect separation. For an active user however, a more secure connection might be required. To insure a more secure mating of the male and female couplers a locking collar 101 shown in FIGS. 23 and 24 is provided. The collar 101 has a plurality of indicator bosses 102 on the entrance face which provide a reference direction as an aid to affixing the locking collar to the female coupler 91 as is further explained with reference to FIG. 25. The locking collar has a snap ring boss 103 at its entrance face, an internal locator boss annulus 104 and a stop ring boss 106 at its end face. As an aid to positioning the collar between a first non-locking position and a second locking position when on the female coupler 91, the locking collar 101 is provided with a gripping annulus 105 on its exterior circumference. FIG. 24 is a cross-sectional view of the locking collar taken along line 24—24.

FIGS. 25 and 26 show locking collar 101 in the unlocked and locked positions respectively in relation to the female coupler 91. Female coupler 91 is aligned with and partially mated with the tapered surface 65 of the male connector 4 which is sealed into the distal end of sheath device 1. A length of fluid tubing 92 is shown connected to the distal end of the female coupler 91. In the unlocked position depicted in FIG. 25, the snap ring boss 103 is located distal to the positioning boss 95 of the female coupler 91. In order to affect a seal and to complete mating of the male and female couplers 4, 91 the female coupler 91 is slid axially over the male coupler 4 until the positioning bosses 64, 95 are coincident. The coupler tangs 93 are free to flex to allow them to bend outwards over the boss 64 of the male coupler 4 as the female coupler 91 is mated with the male coupler 64. The gripping annulus 105 then enables the user to securely grip the locking collar 101 and slide it axially over the positioning boss 95 of the female coupler once the female coupler has been completely engaged with the male coupler 4, placing it in the locked position depicted in FIG. 26. The snap ring boss 103 is now positioned proximal of the outer diameter of the positioning boss 95 of the female coupler 91. When in the locked position, the locking collar 101 prevents the tangs 93 from flexing and this in turn prevents relative movement between the male and female connectors 64, 91. In order to disconnect the couplers, the locking collar 101 must be moved to its unlocked position by sliding it axially in a distal direction.

Figure 27:
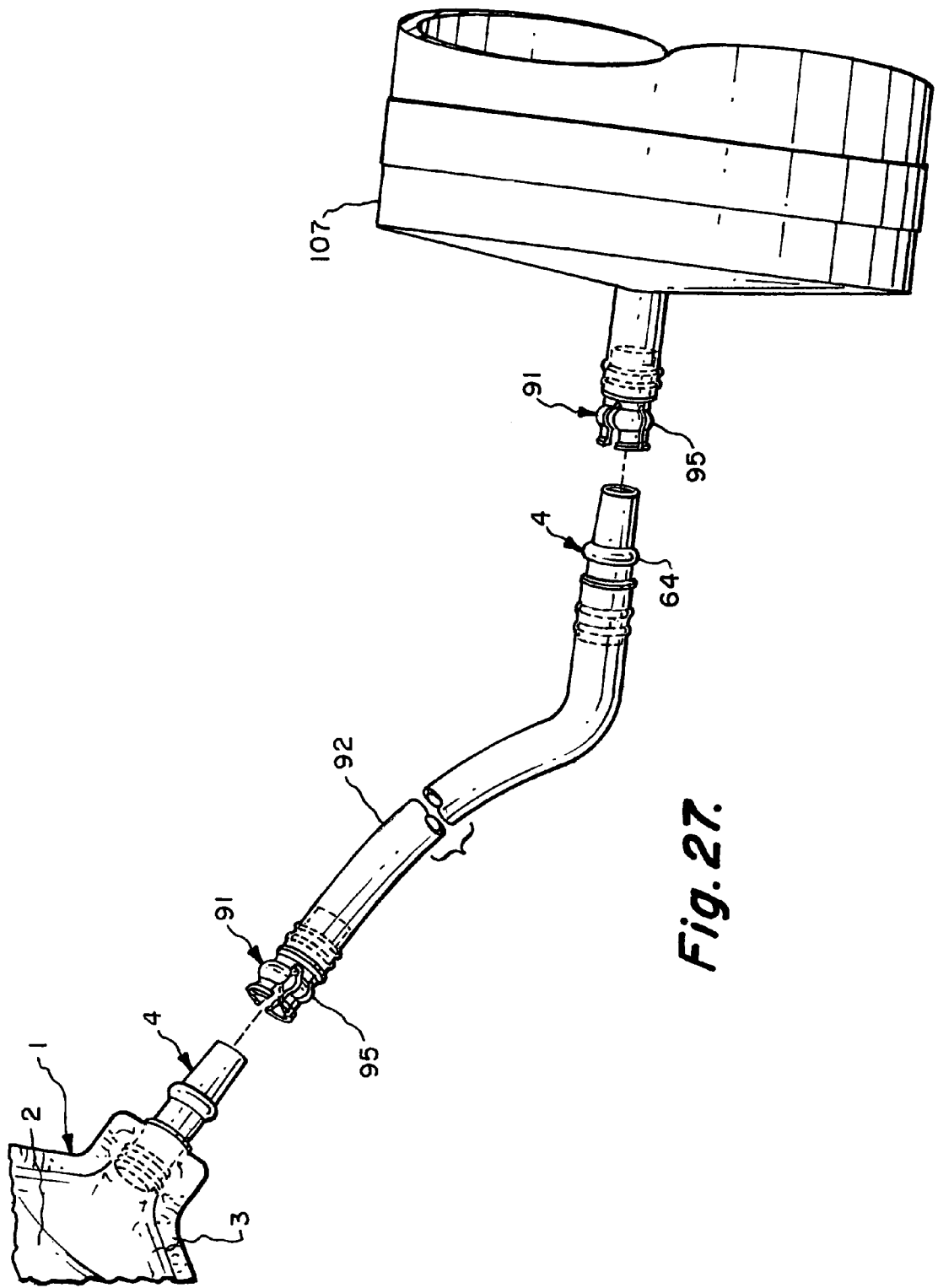
FIG. 27 is an isometric expanded view of a preferred method of connection of the device of FIG. 1 to a collection bag utilizing two male couplers, and two female couplers of FIGS. 6 and 22 respectively.

One of the objects of this invention is to make the connection and disconnection of the sheath of device 1 to a urine storage or collection device easier and more convenient for the user or his care giver. At present, the standard of care in the field of incontinence care is the use of barbed connectors. While the connection of barbed components can be accomplished without a great deal of difficulty, the disconnection of these same components is very difficult due to the barbs and the necessary tight compressive fit of the components. Following the securing of the sheath 1 to the penis of the user, connection of the male connector 4 to a female connector 91 and connection of tubing 92 to a collection bag 107 can take place as shown in FIG. 27. The male coupler 4 and the female coupler 91 have been uniquely designed to connect and disconnect with ease and to securely and releasably mate with each other. They have also been designed to securely and permanently mate with other components required for proper incontinence care.

FIG. 27 depicts a typical assembly of the components allowing the transport of urine from the user into a storage bag. Male coupler 4 is permanently heat sealed into device 1 and may be releasably connected to female coupling 91 permanently connected to tubing 92. Inserted in the distal end of tubing 92 is a second male coupler 4 which is aligned for mating with a second female coupling 91 which may be permanently sealed into the inlet of a collection bag 107.

Figure 28:
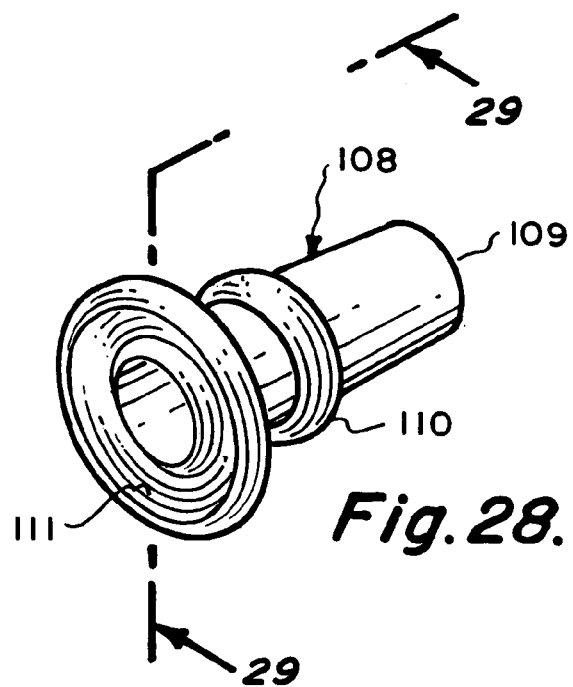
FIG. 28 is an isometric view of a sealing plug for use with the female coupler of FIG. 22.
Figure 29:
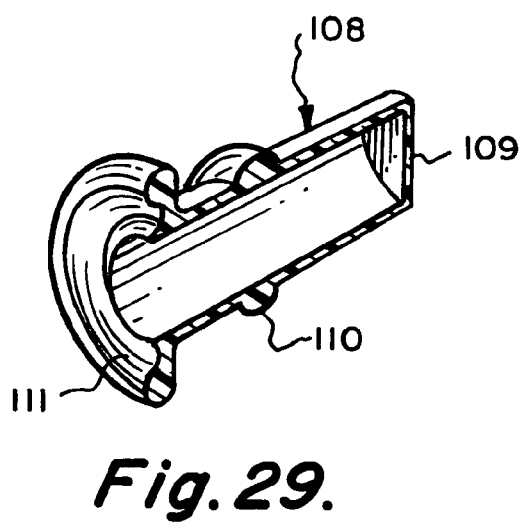
FIG. 29 is a cross sectional view of the sealing plug taken along the line 29—29 of FIG. 28.
Figure 32:
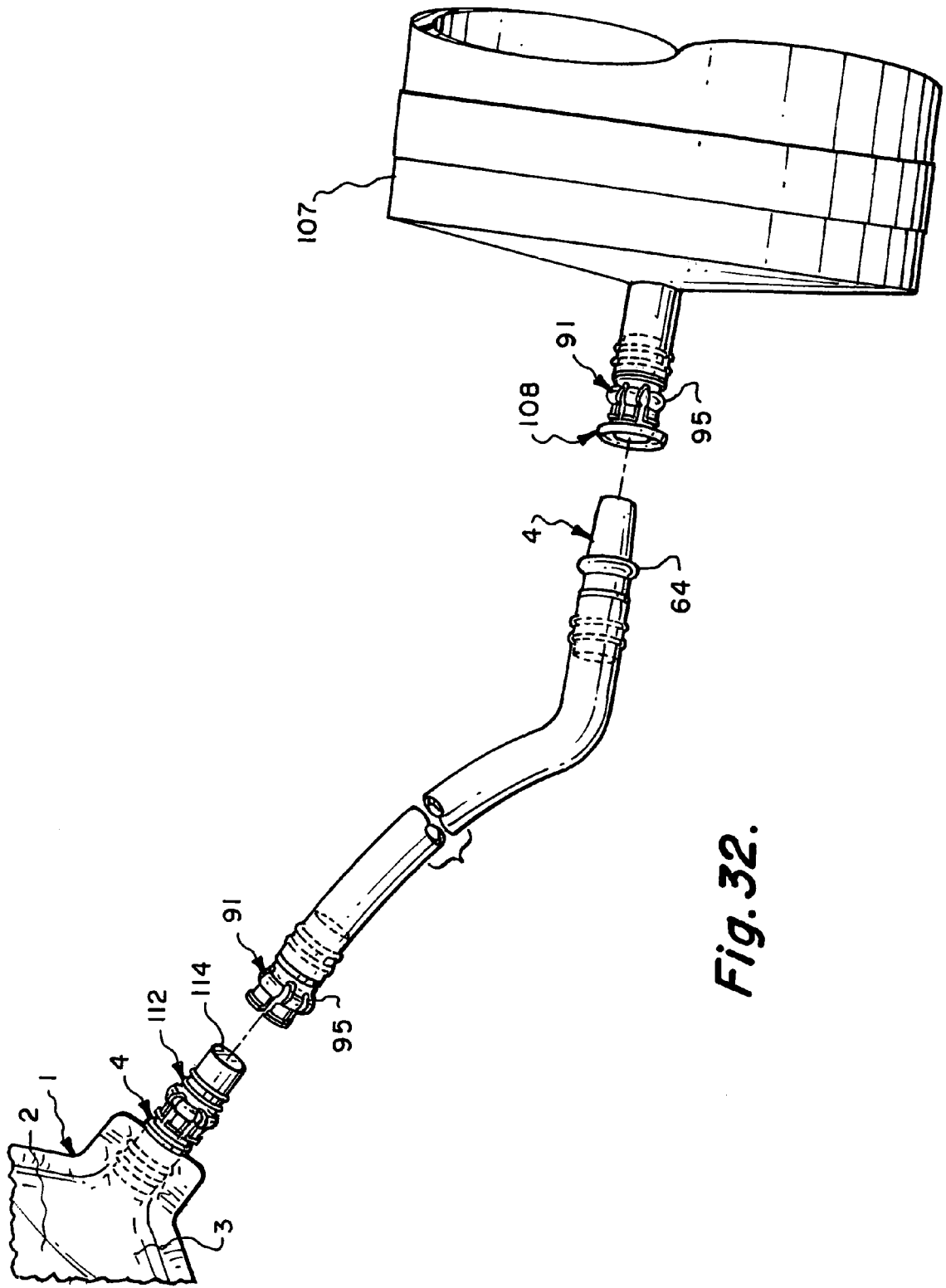
FIG. 32 shows the assembly of FIG. 27 with the female coupler of the collection bag sealed with the sealing plug of FIG. 28 and the male coupler of the sheath sealed with the sealing cap of FIG. 30.

When it becomes necessary to dispose of the contents of storage bag 107 such as depicted in FIG. 27, it is desirable to insure that the collected urine is sealed within the bag. To accomplish this goal, a female coupler plug 108 is provided. The coupler plug 108 has a closed end 109 and a plug positioning boss 110 which mates with the positioning boss 95 of the female coupler 91 as shown in FIG. 32. The plug 108 is also provided with a recessed entrance flange 111 shaped to receive the thumb or finger of the user or caregiver as the plug is pressed into the female coupler to seal the collection bag. FIG. 29, is a section view of plug 108 taken along line 29—29 of FIG. 28 depicting more clearly, the closed end 109 of the plug.

Figure 30:
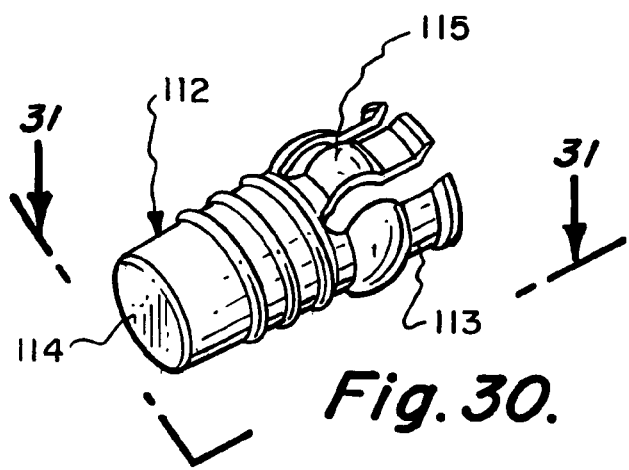
FIG. 30 is an isometric view of a sealing cap for use with the male coupler of FIG. 6.

It may also be necessary to cap the male coupler 4 at the distal end of the sheath device 1 when disposing of the urine in the storage bag 107. To accomplish this goal, a male coupler cap 112 is provided and is depicted in FIG. 30. The coupler cap has a closed end 114 and a cap positioning boss 115 which mates with the positioning boss 64 of the male coupler 4 as is shown in FIG. 32. The cap is pressed onto the male coupler 4 flexing the tangs 113 and reaches its sealing position when positioning boss 115 is coincident with positioning boss 64 of the male coupler 4. As an alternative, if the tubing is not disconnected from the sheath device 1, the sealing cap 114 can be mated to the male coupler 4 at the distal end of tubing 92.

Figure 31:
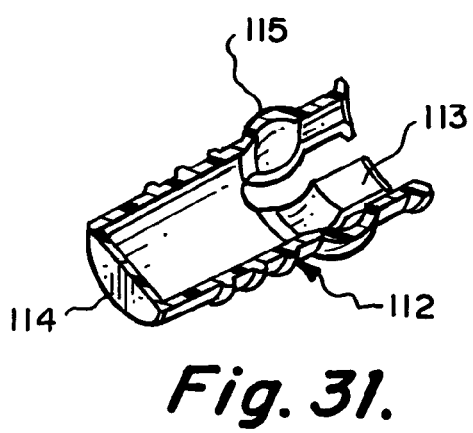
FIG. 31 is a cross sectional view of the sealing cap taken along the line 31—31 of FIG. 30.

FIG. 31 is a section view of cap 112 taken along line 31—31 of FIG. 30 depicting more clearly, the closed end 114 and the positioning boss 115.

FIG. 32 illustrates the male coupler seal cap 112 in position on the male coupler 4 sealed into the sheath device 1 and the female plug 108 in position and sealing the female coupler 91 of storage bag 107.

Figure 33:
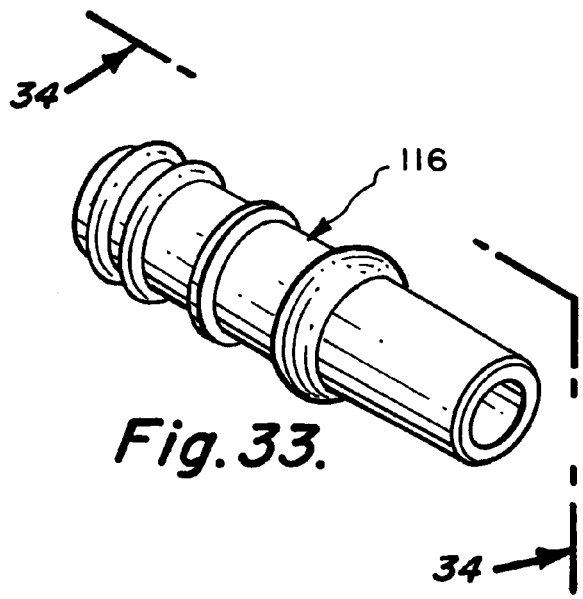
FIG. 33 is an isometric view of an alternative male coupler having an external profile identical to that of the male coupler of FIG. 6.
Figure 34:
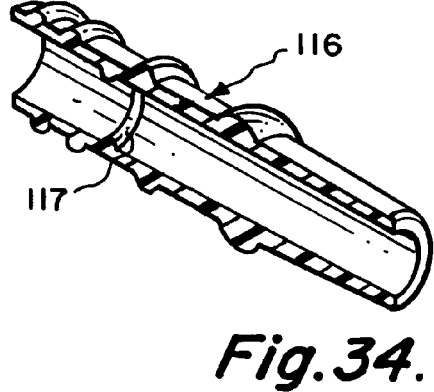
FIG. 34 is a cross sectional view of the alternate male coupler taken along line 34—34 of FIG. 33 showing an internal annular boss.

FIG. 33 shows an alternative male coupler 116, similar to male coupler 4, except that it is provided with an internal boss 117 located near the proximal end of the coupler 116, best shown in FIG. 34 which is a cross sectional view of the alternative male coupler taken along line 34—34 of FIG. 33. The internal boss 117 is provided to serve as a retaining and locating feature for an internal, streamlined, compact one-way flow valve 118 more fully described in FIGS. 35 and 36.

Figure 35:
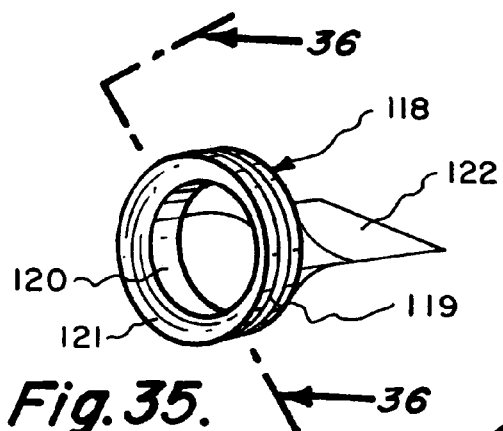
FIG. 35 is an isometric view of a check valve for use within the interior of the male coupler of FIG. 33.

FIG. 35 is an isometric view of a unique, streamlined, compact, injection molded one-way flow valve 118. The material of choice is polypropylene characterized by a high flow-melt index. The valve's cross-sectional area has a rapid transition from the relatively thick section in proximity to the locking grove 119 located distally to the tapered inlet 121 of the valve. The thick cross-section of the valve in the region surrounding the locking grove 119 tapers to the thin outlet leaflets 122 of the distal end. These leaflets 122 are essentially rectangular in cross-section and are very thin, on the order of 0.002 to 0.005 in thickness, and are separated from each other by a leaflet wide opening 123 measuring 0.005 inches or less in height. The leaflets 122 are relatively unwetable by the urine which passes through them, entering the valve at opening 120 and exiting distally through the leaflets. Small droplets of urine however, will form on their surfaces aiding in the function of the valve as explained in reference to FIG. 36

Figure 36:
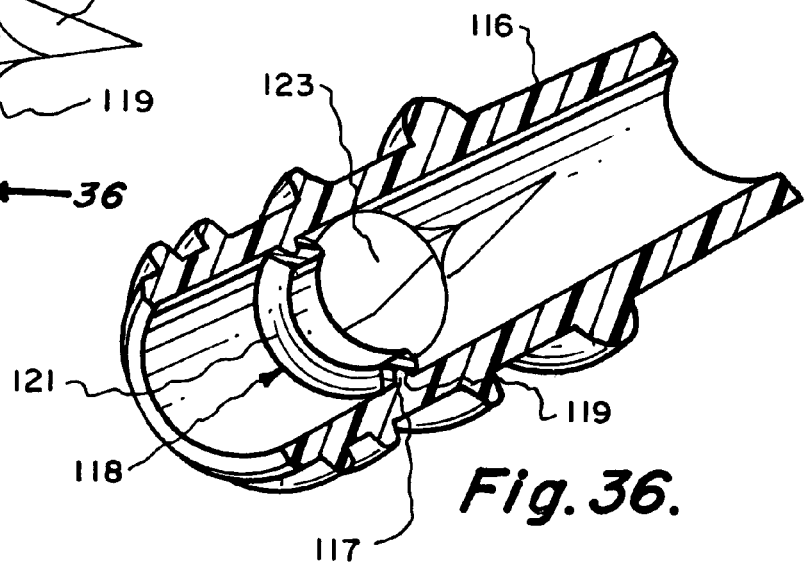
FIG. 36 is a cross sectional view of the check valve taken along line 36—36 of FIG. 35 shown in position on the internal annular boss of the interior fluid channel of the male coupler of FIG. 34.

Operation of the valve 118 is further explained with reference to FIG. 36 which shows the valve body (cross-section, taken along line 36—36 of FIG. 35) fixed in place with locking groove 119 seated on the internal boss 117 of alternative male coupler 116. The tapered inlet allows for smooth flow of urine into the valve opening 120 and prevents the build up of fluid on the face of the valve body. Urine then flows through the leaflet opening 123 and passes through the tube 92 and into storage bag 107 referenced previously. As the leaflets are relatively unwetable, only small droplets of urine will adhere to their surfaces but due to their very thin cross-section, the surface tension of the urine will tend to make the leaflets releasably adhere to each other and in effect, close the valve. If there is a retrograde flow of urine, it will flow against the exterior surfaces of the already closed valve leaflets and further increases of fluid pressure will only serve to keep the leaflets closed and thereby prevent back flow or leakage of the urine.

Reference to FIG. 37 illustrates accessories provided with the sheath device 1 to secure it to body of its user by means of straps 125, 126, 127 (not shown) and 128, which in the preferred embodiment, are made from soft washable cotton material and provide an appropriate closure and adjustment means well known in the medical appliance and clothing industry. Although the polymeric gel strip 22 surrounding the penis of the user in cooperation with the elastomeric adhesive tape 85 wrapped under tension around the exterior of the sheath device 1 provides almost four pounds force of axial resistance to the sheath being pulled off, use of the straps 125, 126, 127, 128 provides even a greater sense of security to the user. In FIG. 37, the penis 89 of the user is seen protruding through a retention ring 124 which is similar in many respects to the retention ring disclosed in U.S. Pat. No. 6,248,096B1. It has however, an important unique and distinguishing feature in that it is provided with a set of right and left cantilever arms 134, 135. These arms are provided with a bulbous tip 137 which in their unflexed or closed position abut the edge 138 of retention ring 124. Left and right waist straps 125, 126 and leg straps 127, 128 are similar to and serve the same function as those described in U.S. Pat. 6,248,096 B1. Two unique VELCRO® securing straps, 129 and 130 have been provided to easily secure the sheath of device 1 to the retention ring cantilever arms 134 and 135. They are identical in design and construction and can be used interchangeably on either the right or left sides. Each strap has a composite tip 136 on it with the inner surface 131of the tip faced with a VELCRO® "hook" fastener which can be secured to the surface of the body of the strap 132 which is faced with a VELCRO® "loop" fastener. The use of these fasteners to releasably secure straps is well known. However the straps of the invention are unique as they are provided with a plurality of preformed attachment openings or loops 133 spaced along the length of the strap. A patient having a relatively long penis would attach the most proximal or end attachment loop over the arms 134 and 135, passing them over the bulbous tip 137. A patient having a shorter penile length would attach the straps using more distally positioned attachment loops. Additional adjustment is made possible by the ability to adhere the hooks 131 at any point on the strap surface 132. Once positioned over the cantilever arms, the straps are prevented from accidentally being dislodged as the cantilever arms 134, 135 are pressed against the edges 138 of the retention ring. The VELCRO® strap tips 136 are designed to readily pass through the slots 19 and 20 on right tab 17 and left tab 18 respectively, of sheath body 2, first identified in FIG. 1.

FIG. 38 depicts the sheath device 1 with the user's penis 89 secured within. The VELCRO® securing strap 129 is shown with tip 136 folded over so that hook fasteners on the tip 136 are attached to the loop fasteners on the surface of strap body 132. Straps 125, 126, 127, 128 are secured to the retention ring 124 and to the patents body as described in U.S. Pat. No. 6,248,096 B1. The male coupler 4 of the sheath device 1 is connected to a female coupler 91 which in turn is connected to the tubing 92 and the collection bag 107.

FIG. 39 depicts a second embodiment of sheath device 1 constructed using the alternate first piece 50 as described with reference to FIG. 4 with the user's penis 89 secured within. The VELCRO® securing straps 129 and 130 are not required to secure this embodiment to the retention ring 124 instead, the tabs 19 and 20 are secured to the retention ring 124 by passing the loops 259 formed in the tabs when the reinforced segments 52 are heat sealed to the sheath body 259 (reference FIG. 4) over the cantilever arms 134, 135 of the retention ring 124. Alternatively but not shown, the cantilever arms 134, 135 could be passed through the slots 19 and 20 respectively, to secure the sheath to the retention ring. The male coupler 4 of the sheath device 1 is connected to a female coupler 91 which in turn is connected to the tubing 92 and the collection bag 107 in the same way as described with reference to FIG. 38.

Using the device and accessories disclosed in this invention, an incontinent user can be assured of a leak proof system to manage his incontinence with ease, convenience, and at a reasonable cost while avoiding many of the problems associated with latex condoms, indwelling catheters or diapers.

In summary, some of the unique aspects of devices incorporating features of the invention include:

A closed cell foam having a viscous coating on at least one surface, a gel, or any other type viscous, easily releasable, sealing strip fabricated of a material which leaves no or minimal residue when removed, said material conforming and accommodating to the adjustable sizing of the device, to prevent leakage. This wrap around, folding over configuration, ensures a proper fit around the penis, allowing for infinite sizing capabilities within a given minimal and maximum range of the device. This viscous, gelatinous material is adhered to the inner surface of the sheath of the invention. The material may be silicone, gels, or foams which create a seal between the interior surface of the sheath and the skin of the penis.

The various alternative materials of construction may be layered together in different configurations, which may include the laying of the foam, or like material directly on the viscous gelatinous material, or actually combining the two materials together.

The outer tape strip is easily deformable, stretchable foam, polymeric or elastomeric material which compensates for the differences in penile diameters which may occur throughout the period of wear by an individual and is suitable for use by a wide range of users who may have different penile diameters.

The current art incorporates adhesives that are of essentially zero thickness and have little or no capability to fill in the voids or spaces between the sheath and the surface of the penis and does not provide a comprehensive seal nor use any viscous gels, foams, or the like to create a seal. The new device described herein utilizes viscous, deformable gels or the like to create a seal. The unique gel or like materials creates a seal by conforming to the variations of skin texture of the penis and will fill in the wrinkles or folds of the loose skin whether flaccid or firm. The gel, although viscous, easily peels off the skin, leaving no residue and no skin irritation as do current adhesives.

The adhesive properties of the viscous gel strip include high shear strength along the axis of the penis to prevent the sheath or pouch from being easily separated or pulled off or falling off. Previous art discloses glues and adhesives which easily dislodge from the skin of the penis allowing prior art devices to easily fall or slip off. A further defect of prior devices, eliminated by the current design, is that liquid is allowed to get between the skin of the penis and the prior art sheath, further accelerating leakage and the sheath separating from the penile shaft.

The new viscous gel, water resistant foams or the like, allow for a water tight seal under all conditions of change in the penis size during the course of daily activities, which include, sleep, walking, sitting, spontaneous erection of a flaccid penis, lifting and stretching, etc.

The viscous gel strip adhesive has a very low tensile or peeling strength which facilitates easy removal by the user. This provides a quick and painless removal as well as leaving no residual adhesives, glues or the like on the skin of the penis.

The combination of the viscous gel material or the like, with the "compressible medium" is unique in that, depending on the various conditions or configurations of the penis, it provides adjustability, conformity and leak-proof sealing properties.

The ability to apply the device without having to roll it on, slip over, or stretch and pull it up onto the penis is new and unique to this art. The device described and shown allows the penis to be laid in an open cylindrical sheath or pouch before the device is sealed around the penis, a technique which is a new and unique approach to apply a urinary incontinence sheath. The inclusion of foam or gel material for sizing adjustment, or a viscous gel or materials of the like for creating a seal against the penis, whether used separately and alone, or in combination is unique and new.

The ability to insert the head of the penis into a collection device without the shaft of the penis being encased, during insertion, by the sheath material allows for an easier approach for application, as well as accommodating a flaccid organ. The sheath material is then caused to surround the penis by folding, closing the sheath around the penis followed by a final seal or wrap, both of which are not shown in prior art devices.

Two folded release liners are positioned on the viscous gel seal to facilitate simultaneous removal after the penis is position in the sheath, ensuring that the gel is uniformly adhered circumferentially to the penis, starting at the bottom surface thereof. The tack or resistance of the release liners to removal from the gel insures that by removal of the release liners the gel is pressed against the penis.

Perforations on the inner gel side folded elements of the release liner allows viscous gel to extrude therethrough to adhere to the patient side film layer, thus maintaining the inner patient side layer in a coincident relationship with the gel side layer.

A water-tight sheath formed from a heat sealed, preformed pouch formed in combination with a pre-assembled tape or flexible adhesive back tape assembly placed onto the preformed pouch, the tape being applied over a portion of the heat sealed pouch and adhered to the heat sealed portion of the pouch and the collinear edges of the open cylinder. When applied to the penis the combination forms an expandable, water tight sheath in a tubular configuration.

The device incorporates a new and unique quick disconnect assembly. The configuration of the male and female connectors provides for easy attachment to extension tubings, or to leg bags, or bedside drain bags, etc. This connector arrangement is not limited to the disclosed device but may be incorporated in various different fluid flow systems in which a liquid-tight quick and clean disconnect and reconnect is desired including, including but not limited to other urine collection assemblies and devices such as catheters, thereby reducing the risk of urinary tract infections (UTI), urine drainage devices, various body fluid collection or delivery bags, containers, or the like. This connector can be used with many configurations of tubing which require connection and disconnection on a routine basic. This includes intravenous lines, medication lines and catheter lines to include urostomy. Further, the locking collar prevents the male and female halves of the connector set from accidentally disconnecting The use of a strap attached between the sheath, pouch, or the like, and the face plate provides added security of attachment of the sheath, pouch, or the like, minimizing the likelihood of the device falling off or disengaging from the penis.

The inclusion of an anti-reflux valve into the device or as an attachment to the end of the device prevents the back flow of fluid.

The use of a leg strap which is attached to the face plate for securing the device to the body, with the leg strap wrapped around the thigh of the user, i.e., not passing between the legs and going up through the crotch and attached to the waist band, is new and unique arrangement.

The doubled-over, heat sealed end of the sheath device has stiffness built in to provide an easier entry of the head of the penis to the device, as well as providing additional support for the head of the penis and the penile shaft. This also provides greater comfort to the user.

The doubled-over, heat sealed tabs of the sheath device form loops which permit the device to be attached directly to the cantilever arms of the face plate without the need for additional straps The face plate has recesses for belts and straps so they do not contact and cause irritation to the skin of the user when it is in contact with the skin. The faceplate also has cantilever arms for easy attachment of the waistband and to facilitate a stable placement of the bands.

One skilled in the art will recognize that, based on the above descriptions various modifications in the sheath construction and its method of fabrication may be adapted. For example, an option is to not fully heat seal the device so that it has the form of a trough or base assembly for application. A trough would have the device completely open Unsealed along a longitudinal edge. For application of the device the penis would be laid on the open device with the glans inserted into the distal end. The device would then be folded over the penis and sealed along the open edge using various folding and adhesive techniques to form a cylindrical sheath followed by sealing of the device around the penile organ as previously herein described. Once the device encases the penis, in any of the above mentioned configurations, the adjustability for firming or tightening the device for a water tight and comfortable seal can be accomplished by rolling, folding, turning, or any method of decreasing the looseness of the device around the penile shaft in order to create a waterproof seal, and then sealing the flap or fold or the like to the outer material of the device. Alternatively the device can be secured to the penis not only by having the gel, foam, or the like, but additionally by securing the device circumferentially by wrapping and elastic band that adheres to it by various methods, which may include VELCRO®, tacky adhesives, clips, or any method of securing the wrap to it.

As a further alternative, the nozzle may be offset downward from the central axis of the sheath. This offset of the nozzle to the lower end at the distal end of the device will assure that when urine is expelled or released it will flow out at the lowest end of the device. By positioning the nozzle opening lower than the middle of the distal end of the device there is less chance of urine pooling in any open space in the distal end off the sheath which is not filled by the penile gland. Also the internal configuration of the sheath which contacts the penile glans or the end of the penis may be modified by providing the material of construction with ripples, forming a wavy appearance, or grooves, or the like to direct the urine flow to the offset nozzle opening. This configuration would offset the outlet tube from the orifice opening of the penis so as not to occlude it and to prevent urine from flowing out of the penis. It is also possible to construct the sheath of a non-wetable but porous material, with minimal elasticity that would allow for air exchange, yet not allow fluid to pass through the pores of the material. This approach would decrease the potential for irritation or excoriation of the skin of the penis.

We claim:

1. A device for attachment to the penis of an individual for receiving urine and delivering the urine to a collection chamber, the device comprising a sheath non-permeable to urine, the sheath being cylindrically shaped when fully applied to the penis, the cylindrical sheath having an inner surface and an outer surface and a first end and a second end at opposite ends of the cylindrical sheath and having:

an opening in the first end of the cylindrical sheath sized to receive at least a portion of the length of a penis, the second end of the cylindrical sheath, spaced longitudinally along a central axis of the cylindrical sheath from said first end, including a hollow connector sealed therein, the hollow connector configured to mate with a second hollow connector attached to the collection chamber, the distance between the first end and the second end being sufficient to enclose at least the glans of the penis and carry a first securement means on the inner surface and a second securement means on the outer surface at the first end, the first and second securement means encircling the penis above the glans, the first securement means comprising a compliant, viscous, stretchable and conformable polymeric gel strip and the second securement means comprising an elastic securement tape, the sheath having an upper portion with a longitudinal opening extending from the opening in the first end at least partially along the length of the sheath toward the second end, the polymeric gel strip adhesively attached to an upper circumferential portion of the inner surface of the sheath adjacent the opening in the first end of the sheath, the gel strip comprising a compliant, viscous stretchable and conformable polymeric gel material impervious to urine, resistant to swelling, absorption, erosion, permeation when exposed to urine and inherently adherent to skin surfaces, the gel strip having, on a sheath contacting surface, a double sided adhesive strip comprising a first adhesive which bonds to the gelatinous polymeric material and a second adhesive which bonds to the inner surface of the sheath, the double sided adhesive strip function to permanently secure the gelatinous polymeric material to the sheath; having a skin contact surface which provides adhesion to the skin surface of the penis but is readily removable there from without leaving residual gel material on the surface of the penis, the gel material being stretchable and contractible after application to the penis to an extent substantially similar to changes in circumference or length of the penis after application without compromising adhesion to the sheath or penile skin surface or allowing urine leakage, said gel strip skin contact surface having a removable barrier material covering said contact surface, the barrier removable during placement of the sheath on the penis, the elastic securement tape having a first end attached to an upper circumferential portion of the outer surface of the sheath adjacent the first end opening of the sheath, the tape oriented to be wrapped circumferentially around the sheath, said securement tape having attachment means extending along the length of an inner surface thereof so that upon wrapping said tape around the upper circumferential surface of the sheath the tape becomes adhered to the sheath, secures the sheath to the penis placed therein and closes the opening extending longitudinally from the first open end at least a portion of the distance between the first end and the second end in a leak proof manner.

2. The device of claim 1 further including slotted tabs extending from an upper edge of the sheath, each of said slotted tabs configured to receive one or more adjustable straps there through, the adjustable straps also passing through slots in a ring encircling the base of the penis.

3. The device of claim 2 wherein the ring is retained on the individual by multiple belts encircling the waist and thighs of the individual.

4. The device of claim 1 wherein the hollow connector comprises a tubular male coupling of a predetermined outer diameter an intermediate portion of the outer surface of the coupling having a raised boss encircling the connector, the tubular mail coupling being sized to be received within the second hollow connector attached to the urine collector.

5. The device of claim 4 wherein the second hollow connector is a tubular female coupler having two or more longitudinal slots along a portion of a first end thereof forming outwardly tapering tangs there between and an intermediately positioned, internally concave positioning boss, the inner diameter of the tubular female coupler and internally concave positioning boss sized to mate with the male coupling in a leak-proof manner, the second end of the female coupler being attached to the urine collection chamber.

6. The device of claim 5 wherein the urine collection means comprises tubing attached to a urine collection container, the tubing also being attached to a second end of the female coupler.

7. The device of claim 5 further including an encircling, sliding locking collar sized for locking placement over the boss on the male coupler and the female coupling after engagement thereof.

8. The device of claim 1 further including a one way flow valve positioned at or below the second end of the sheath, the one way valve configured to allow urine to flow from the sheath to the collection chamber but to prevent urine from flowing from the collection chamber into the sheath.

9. The device of claim 8 wherein the one way valve includes first and second flat leaflet portions, said leaflet portions positioned at their lower end in contact each other for urine to flow between the leaflets and through said lower end.

10. The device of claim 8 wherein the one way flow valve is positioned within a lumen of the hollow connector.

11. The device of claim 1 wherein the gelatinous polymeric material comprises a 2-component silicone material.

12. The device of claim 1 wherein the polymeric gel material has a modulus of elongation and a shear strength such that the gel material will elongate an amount equal to expansion of the penis during normal usage without the gel material separating, the adhesion to the skin is not compromised and leakage is prevented.

13. The device of claim 1 wherein the removable barrier material covering the gel strip skin contact surface has perforations therein which allow penetration of the gel material there through prior to removal of the barrier material for application to a skin surface.

14. The device of claim 1 wherein the elastic securement tape comprises an elastic, polymeric base material having an adhesive on a sheath contacting surface for attaching the securement tape to the outer surface of the sheath.

* * * * *